United States Patent
Reddy et al.

(10) Patent No.: US 8,435,459 B2
(45) Date of Patent: May 7, 2013

(54) HEATING AND STERILIZING APPARATUS AND METHOD OF USING SAME

(75) Inventors: Ganta S. Reddy, Cincinnati, OH (US); Ramgopal Vissa, Hyderbad (IN); Jaingesh A. Sekhar, Cincinnati, OH (US)

(73) Assignee: Micropyretics Heaters International, Inc., Cincinnati, OH (US)

( * ) Notice: Subject to any disclaimer, the term of this patent is extended or adjusted under 35 U.S.C. 154(b) by 674 days.

(21) Appl. No.: 12/514,516

(22) PCT Filed: Nov. 14, 2007

(86) PCT No.: PCT/US2007/084670
§ 371 (c)(1),
(2), (4) Date: Feb. 5, 2010

(87) PCT Pub. No.: WO2008/061139
PCT Pub. Date: May 22, 2008

(65) Prior Publication Data
US 2010/0129157 A1 May 27, 2010

Related U.S. Application Data

(63) Continuation-in-part of application No. 11/682,107, filed on Mar. 5, 2007, now Pat. No. 8,119,954, which is a continuation-in-part of application No. 10/703, 497, filed on Nov. 10, 2003.

(60) Provisional application No. 60/935,967, filed on Sep. 7, 2007, provisional application No. 60/935,160, filed on Jul. 27, 2007, provisional application No. 60/929,637, filed on Jul. 6, 2007, provisional application No. 60/249,958, filed on Jun. 6, 2007, provisional application No. 60/907,944, filed on Apr. 24, 2007, provisional application No. 60/901,007, filed on Feb. 13, 2007, provisional application No. 60/858,944, filed on Nov. 15, 2006, provisional application No. 60/832,608, filed on Jul. 24, 2006, provisional application No. 60/438,321, filed on Jan. 7, 2003.

(51) Int. Cl.
*A61L 2/00* (2006.01)
*F22B 37/00* (2006.01)
*A45D 20/10* (2006.01)

(52) U.S. Cl.
USPC ............................ 422/292; 122/5.51; 392/383

(58) Field of Classification Search .................. 422/292
See application file for complete search history.

(56) References Cited

U.S. PATENT DOCUMENTS 3,039,454 A * 6/1962 Gilbertson et al. .... 126/271.2 R
(Continued)

FOREIGN PATENT DOCUMENTS

WO WO2008061137 5/2008
WO WO2008061139 5/2008

OTHER PUBLICATIONS

M. Fu, Kandy Staples and Vijay Sarvepalli; A High Capacity Melt Furnace for Reduced Energy Consumption and Enhanced Performance. Journal of Metals (JOM), May 1998, p. 42-44.
(Continued)

*Primary Examiner* — Kevin Joyner
(74) *Attorney, Agent, or Firm* — Michael C. Connelly

(57) ABSTRACT

An apparatus (200, 300, 400) for generating superheated steam capable of reducing or eliminating microorganisms associated with an item (230) includes a gas heater (10) for heating a gas, a steam generator coupled to the gas heater (10) and having a reservoir (216, 304) for supplying water, wherein the heater (10) heats the gas such that when water is combined therewith, a mixture of superheated steam and gas capable of reducing or eliminating microorganisms is discharged from the apparatus (200, 300, 400). The generation of the steam-gas mixture may be done at one atmosphere of pressure and the mixing may be done prior to expelling the fluid from the apparatus (200, 300, 400). The apparatus (400) may be configured as a hand-held device, A method of treating an item (230) for microorganisms includes generating a superheated steam at approximately one atmosphere of pressure, directing a flow of the steam onto the item (230), and reducing or eliminating microorganisms using the steam.

10 Claims, 14 Drawing Sheets

U.S. PATENT DOCUMENTS

| | | | | |
|---|---|---|---|---|
| 3,258,578 | A | * | 6/1966 | Ferris ............................ 392/404 |
| 3,718,805 | A | * | 2/1973 | Posey ............................ 392/397 |
| 4,149,104 | A | | 4/1979 | Yoshimori |
| 4,350,872 | A | | 9/1982 | Meywald et al. |
| 4,794,255 | A | | 12/1988 | Miyatake |
| 5,655,212 | A | | 8/1997 | Sekhar et al. |
| 5,766,458 | A | | 6/1998 | Sekhar et al. |
| 5,963,709 | A | * | 10/1999 | Staples et al. ................. 392/488 |
| 2002/0100433 | A1 | * | 8/2002 | Uchiyama .................... 122/459 |
| 2004/0134480 | A1 | | 7/2004 | Vissa et al. |
| 2007/0145038 | A1 | | 6/2007 | Vissa et al. |
| 2010/0150775 | A1 | | 6/2010 | Reddy et al. |

OTHER PUBLICATIONS

"International Application Serial No. PCT/US07/84670, International Search Report", issued Sep. 22, 2008, 8 pgs.

"International Application Serial No. PCT/US07/84670, International Preliminary Report on Patentability" issued May 19, 2009, 11 pgs.

"International Application Serial No. PCT/US07/84670, Written Opinion", issued May 15, 2009, 10 pgs.

M. Fu, Kandy Staples and Vijay Sarvepalli; Convective Heating Below 1000C. Advanced Materials and Processing Magazine, Oct. 1999, pp. 213-215.

* cited by examiner

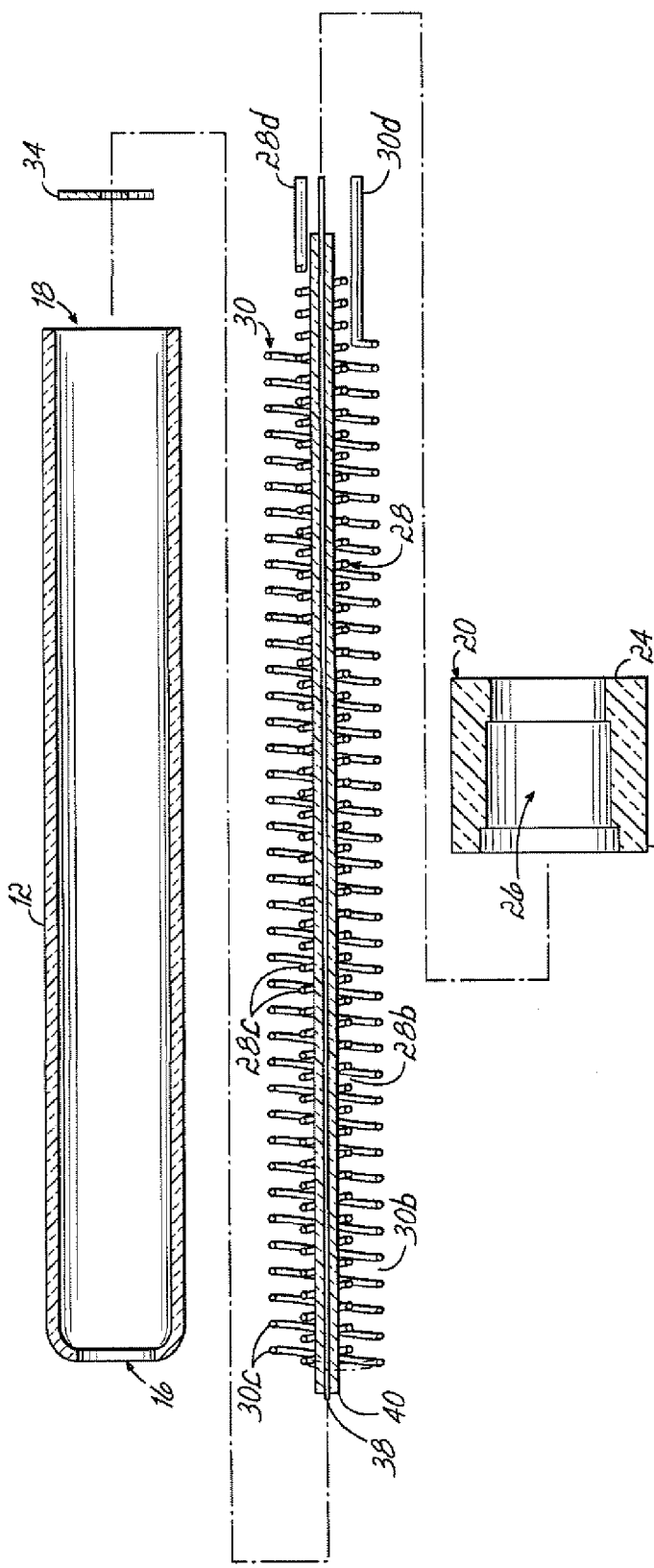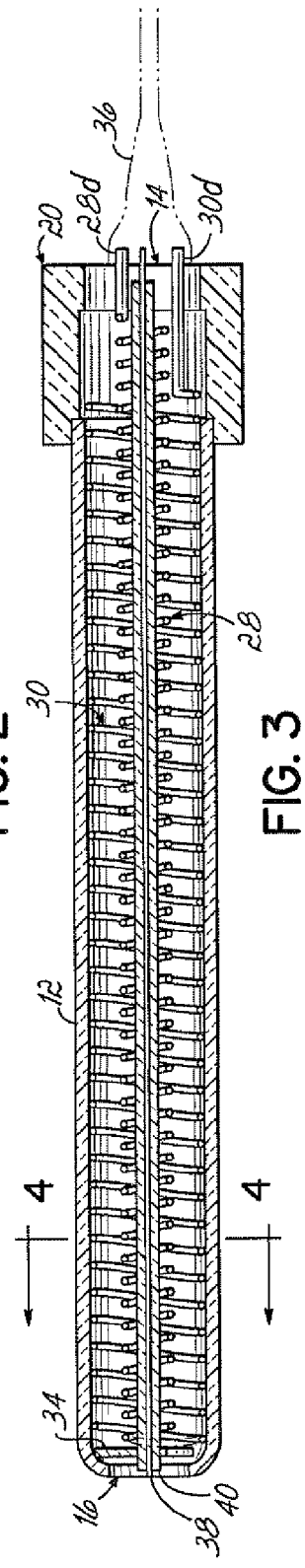
FIG. 2
FIG. 3

US 8,435,459 B2

HEATING AND STERILIZING APPARATUS AND METHOD OF USING SAME

CROSS-REFERENCE TO RELATED APPLICATIONS

This is a continuation-in-part application of U.S. patent application Ser. No. 11/682,107, now U.S. Pat. No. 8,119,954 filed on Mar. 5, 2007, which claimed the benefit of U.S. Provisional Patent Application Ser. No. 60/832,608 filed on Jul. 24, 2006; which is a continuation-in-part application of U.S. patent application Ser. No. 10/703,497 filed on Nov. 10, 2003, which claimed the benefit of U.S. Provisional Patent Application Ser. No. 60/438,321 filed on Jan. 7, 2003, each of which is hereby incorporated by reference herein in its entirety. This application also claims the benefit of U.S. Provisional Application Ser. No. 60/858,944 filed on Nov. 15, 2006; U.S. Provisional Application Ser. No. 60/901,007 filed on Feb. 13, 2007; U.S. Provisional Application Ser. No. 60/907,944 filed on Apr. 24, 2007; U.S. Provisional Application Ser. No. 60/924,958 filed on Jun. 6, 2007; U.S. Provisional Application Ser. No. 60/929,637 filed on Jul. 6, 2007; U.S. Provisional Application Ser. No. 60/935,160 filed on Jul. 27, 2007; and U.S. Provisional Application Ser. No. 60/935,967 filed on Sep. 7, 2007, each of which is hereby incorporated by reference herein in its entirety. This application is also related to PCT Application No. PCT/US2007/084667, filed on Nov. 14, 2007, the disclosure of which is also hereby incorporated by reference herein in its entirety.

BACKGROUND OF THE INVENTION

Heating of liquids and gases (e.g., fluids) can be carried out by a variety of techniques including conduction, radiation and convection and this heat may be transferred to other objects in thermal communication with the heated fluid. A wide variety of thermal processing applications for heating are found throughout industry including materials processing and chemical applications. The industrial process of heat-treating, joining, curing and drying are carried out in many different types of systems, furnaces and ovens. The heating method of choice for such applications is normally a radiative technique with radiant electric heating elements placed along the walls of the furnace. Although such a method is efficient for very high temperature applications, the use of convection as the heat transfer mechanism often proves to be efficient in the lower temperature ranges. The following prior art patents all pertain to various methods of heating gases; namely, U.S. Pat. Nos. 5,766,458; 5,655,212 and 5,963,709. Discussions on convective heating are available from (1) M. Fu, Kandy Staples and Vijay Sarvepalli. A High Capacity Melt Furnace for Reduced Energy Consumption and Enhanced Performance. Journal of Metals (JOM), May 1998, pg 42 and (2) *ADVANCE MATERIALS & PROCESSES* magazine (pages 213 to 215, October, 1999).

The proper selection of thermal heating for industrial applications such as processing ovens and furnaces is a critical decision to meet the needs of almost all engineering products during their manufacture. The considerations of heating devices and techniques are much different for such industrial applications compared to residential or consumer applications such as hair dryers, hot air popcorn poppers and the like, examples of which are disclosed in U.S. Pat. Nos. 4,350,872; 4,794,255 and 4,149,104. The differences are largely due to the vastly divergent temperature, pressure and airflow requirements. Oven and furnace design for industrial applications must take into consideration heat transfer methods, the temperature uniformity, movement of the product, atmosphere, construction and the heat generation method. Heat processing equipment is usually classified as ovens operating to 1000° C. and as furnaces above this temperature. Batch and continuous designs are the common choices depending on the flexibility and productivity requirements. The source of heat is normally provided by oil, gas or electricity.

Gas heating techniques include natural convection, forced convection and radiation. Natural convection is slow and not very uniform. Forced convection on the other hand is easily controllable and can be directed for odd shapes. Radiant heat transfer at higher temperatures may be faster for some products, but may contribute other problems to the process like non-uniformity and distortion, to mention a few. Forced convection offers advantages over radiant heating for a number of industrial applications. Forced hot convection is also used for fuel cells, automobile test beds and product qualifications.

SUMMARY OF THE INVENTION

These and other problems in the prior art have been addressed by this invention which, in one embodiment, is an industrial gas heater having a tubular enclosure with a gas entry port spaced from a gas exit port. The industrial gas heater, in various embodiments, includes an inner helical coil contained within the tubular enclosure and an outer helical coil also contained within the tubular enclosure and surrounding the inner coil to define a substantially unobstructed annular space between the coils. Each coil is electrically heated to convectively heat a gas entering the tubular enclosure via the gas entry port, passing through the annular space between the coils and exiting the tubular enclosure via the gas exit port. At least a portion of at least one of the inner or outer coils may be coiled itself.

In various other embodiments according to this invention, the inner and outer coils are each right circular helical coils and are arranged concentrically. The inner and outer coils may be wound in opposite directions from each other or in the same direction. The individual coils may be formed from a generally continuous wire concentrically wound into a right circular helical coil. In other embodiments of this invention, the inner and outer coils may have different configurations from one another. A spacer may be positioned within the tubular enclosure and proximate the gas exit port and adjacent distal ends of the inner and outer coils to minimize deformation of the coils.

The tubular enclosure may be a housing in the form of a right circular cylinder having an open end proximate the gas entry port and an end cap closes the open end of the housing. In various embodiments of this invention, the outer coil is positioned in close proximity to or in contact with an inner surface of the tubular enclosure to minimize gas flow between the outer coil and the inner surface of the tubular enclosure and to maximize heat transfer to the gas.

Since some embodiments in accordance with the invention are intended for industrial applications, the inner and outer coils are adapted to heat the gas flowing through the annular space and exiting the gas exit port to a temperature in the range of 500° C. to about 1500° C. and at a rate in the range of about 1 cubic foot per minute (CFM) to about 1000 CFM.

In another embodiment of this invention, multiple of the industrial gas heaters are arranged and mounted in a sealed gas flow chamber. In a further modification, each of the wires utilized for the coils in the gas heaters are themselves configured as coils. Moreover, the industrial gas heater of this invention may be utilized to generate super-saturated steam.

This invention also includes a method for heating a gas for industrial applications including the steps of introducing the gas into a tubular enclosure through an entry port and then flowing the gas through a substantially unobstructed annular space within the tubular enclosure and between inner and outer helical coils. The helical coils are electrically heated to heat the gas flowing therethrough. The gas is then expelled out of the tubular enclosure through an exit port at a temperature in the range of 500° C. to about 1500° C. and at a rate in the range of about 1 CFM to about 1000 CFM. In various other embodiments of this method, the gas is rifled or spiraled between adjacent turns of the inner and outer coils to increase the heat transfer to the gas. The inner and outer coils may be oppositely wound from one another so that the gas spiraling between the adjacent turns of the inner coil is in the direction opposite the gas spiraling between the adjacent turns of the outer coil to thereby increase the heat transfer to the gas.

In another embodiment, an industrial superheated steam generator includes a fluid reservoir adapted to contain a working fluid, a mixing device in fluid communication with the fluid reservoir, a gas heater adapted to heat a gas and in fluid communication with the mixing device, and a reactor vessel in fluid communication with the mixing device to receive a fluid and heated gas mixture to produce superheated steam exiting the reactor vessel. In one embodiment, the gas heater includes a tubular enclosure having a gas entry port spaced from a gas exit port, an inner helical coil within the tubular housing, an outer helical coil in the tubular enclosure and surrounding the inner coils to define a substantially unobstructed annular space therebetween. Each coil is electrically coupled to heat a gas entering the tubular enclosure gas entry port, passing through the annular space, and exiting the tubular enclosure via the gas exit port. Moreover, in one embodiment, the mixing device may be a venturi mixing device.

One exemplary application for aspects of the invention is directed to microorganism management. An apparatus for generating superheated steam capable of reducing or eliminating unwanted microorganisms associated with an item includes a gas heater for heating a gas, and a steam generator operatively coupled to the gas heater and including a fluid reservoir for supplying water to the apparatus. The gas heater heats the gas to a temperature above the saturation temperature of the water such that when the water is combined with the heated gas, a mixture of superheated steam and gas capable of reducing or eliminating microorganisms may be discharged from the apparatus. The generation of the superheated steam-gas mixture is done at approximately one atmosphere of pressure. Moreover, the temperature of the steam-gas mixture may be between the saturation temperature of water at about one atmosphere of pressure (e.g., about 100° C.) and 1,500° C. In one embodiment, the gas heater includes a tubular enclosure having a gas entry port spaced from a gas exit port, an inner helical coil within the tubular housing, an outer helical coil in the tubular enclosure and surrounding the inner coils to define a substantially unobstructed annular space therebetween. In one embodiment, the steam generator may include a reactor vessel for mixing the water from the reservoir with the heated gas from the gas heater so as to generate the superheated steam-gas mixture. In an alternative embodiment, the steam generator may include a jacketed housing disposed about at least a portion of the gas heater and in thermal communication therewith. The housing defines a chamber having an inlet in communication with the reservoir and an outlet in communication with the heated gas. A pump may supply water to the apparatus and may also meter or control the flow rate thereto.

Various advantages afforded by aspects of the invention allow the apparatus to be presented in a hand-held platform. To this end, a hand-held apparatus for generating superheated steam capable of reducing or eliminating unwanted microorganisms include a housing member having an upper housing portion and a handle portion adapted to be grasped by a user. A heater and steam generator assembly sized to be used with such a hand-held device includes a first end coupled to the housing member and a second end projecting therefrom. The heater and steam generator assembly includes a gas heater for heating a gas, and a steam generator operatively coupled to the gas heater and including a fluid reservoir for supplying water to the apparatus. The hand-held apparatus may further include a fan for supplying environmental air to the gas heater and a heat shield surrounding at least a portion of the heater and steam generator assembly.

In still a further embodiment, an apparatus for generating a superheated fluid capable of reducing or eliminating unwanted microorganisms associated with an item includes a gas heater, and a superheat fluid generator operatively coupled to the gas heater and including a fluid reservoir for supplying a working fluid to the apparatus. The gas heater heats the gas to a temperature above the saturation temperature of the working fluid such that when the working fluid is combined with the heated gas, a mixture of superheated vapor of the working fluid and gas capable of reducing or eliminating microorganisms may be discharged from the apparatus. The generation of the superheated vapor-gas mixture occurs internal to the apparatus. In this way, the concentration of the superheated vapor in the mixture is no more than approximately 30% so as to more efficiently use the vapor for sterilizing or disinfecting purposes.

A method of treating an item for microorganisms includes generating superheated steam at approximately one atmosphere of pressure, directing a flow of the superheated steam onto the item, and reducing or eliminating unwanted microorganisms associated with the item using the superheated steam. In one embodiment, the generating step may include introducing a gas into a gas heater, heating the gas to a temperature above the saturation temperature of water at approximately one atmosphere of pressure, and introducing water into the heated gas so as to produce a mixture of superheated steam and gas. The introducing and heating steps may include introducing a gas into a tubular enclosure through an entry port of the enclosure, flowing the gas through a substantially unobstructed annular space within the tubular enclosure and between inner and outer coils, electrically heating the inner and outer coils, and expelling the gas out of the tubular enclosure through an exit port in the enclosure spaced from the entry port. In various embodiment, a pump may be used to supply the water to the device and a fan may be used to supply air to the heater.

In another embodiment, a method of treating an item for microorganisms includes generating a mixture of a superheated fluid with a gas within an apparatus, expelling the mixture of the superheated fluid and gas from the apparatus, directing the flow of the mixture onto the item, and reducing or eliminating unwanted microorganisms associated with the item using the mixture. The concentration of the superheated fluid in the mixture may be no more than approximately 30%.

Another application of aspects of the invention may be directed to the treatment of plant life for various agriculture and horticulture purposes. To this end, a method of treating soil for microorganisms includes generating superheated steam at approximately one atmosphere of pressure, directing a flow of the superheated steam into the soil, and reducing or eliminating microorganisms associated with the soil using the superheated steam. The generating step may include introducing a gas into a gas heater, heating the gas to a temperature above the saturation temperature of water at approximately one atmosphere of pressure, and introducing water into the heated gas so as to produce a mixture of superheated steam and gas. An adaptor may be provided having an end suitable for penetrating soil.

In a further embodiment for treating plant life, an apparatus for reducing or eliminating unwanted microorganisms in soil includes a frame member adapted to be coupled to a vehicle for moving the apparatus of soil, at least one rotatable disk coupled to the frame and having a plurality of radially extending fingers, and a heater and steam apparatus mounted to the frame for generating a flow of superheated steam. The heater and steam apparatus is in fluid communication with each of the fingers such that superheated steam flows into the soil when the fingers are embedded therein.

As a result, a convective heating system and associated method for heating a gas for industrial applications are provided that overcome many of the shortcomings associated with known systems and techniques in the prior art. Additionally, apparatus and methods for microorganism management are provided that overcome many of the shortcomings with known apparatus and methods in the prior art.

BRIEF DESCRIPTION OF THE DRAWINGS

The above-mentioned and other features and advantages of this invention, and the manner of attaining them, will become more apparent and the invention itself will be better understood by reference to the following description of embodiments of the invention taken in conjunction with the accompanying drawings, wherein:

FIG. 2 is a disassembled side elevational view of the heating system of FIG. 1;

FIG. 3 is an assembled side elevational view of the heating system of FIG. 2;

FIG. 16 is a graph which provides exemplary data of how to adjust the system 200 of FIG. 7 for different levels of specific humidity.

DETAILED DESCRIPTION OF THE INVENTION

This invention provides a new technique for very low cost convective, wet and dry heat generation. One aspect of the invention is to heat the air or gas through a concentric energized heating coil system. We have found that the concentric design heats the gas to a more consistent temperature in an energy efficient manner.

Figure 1:
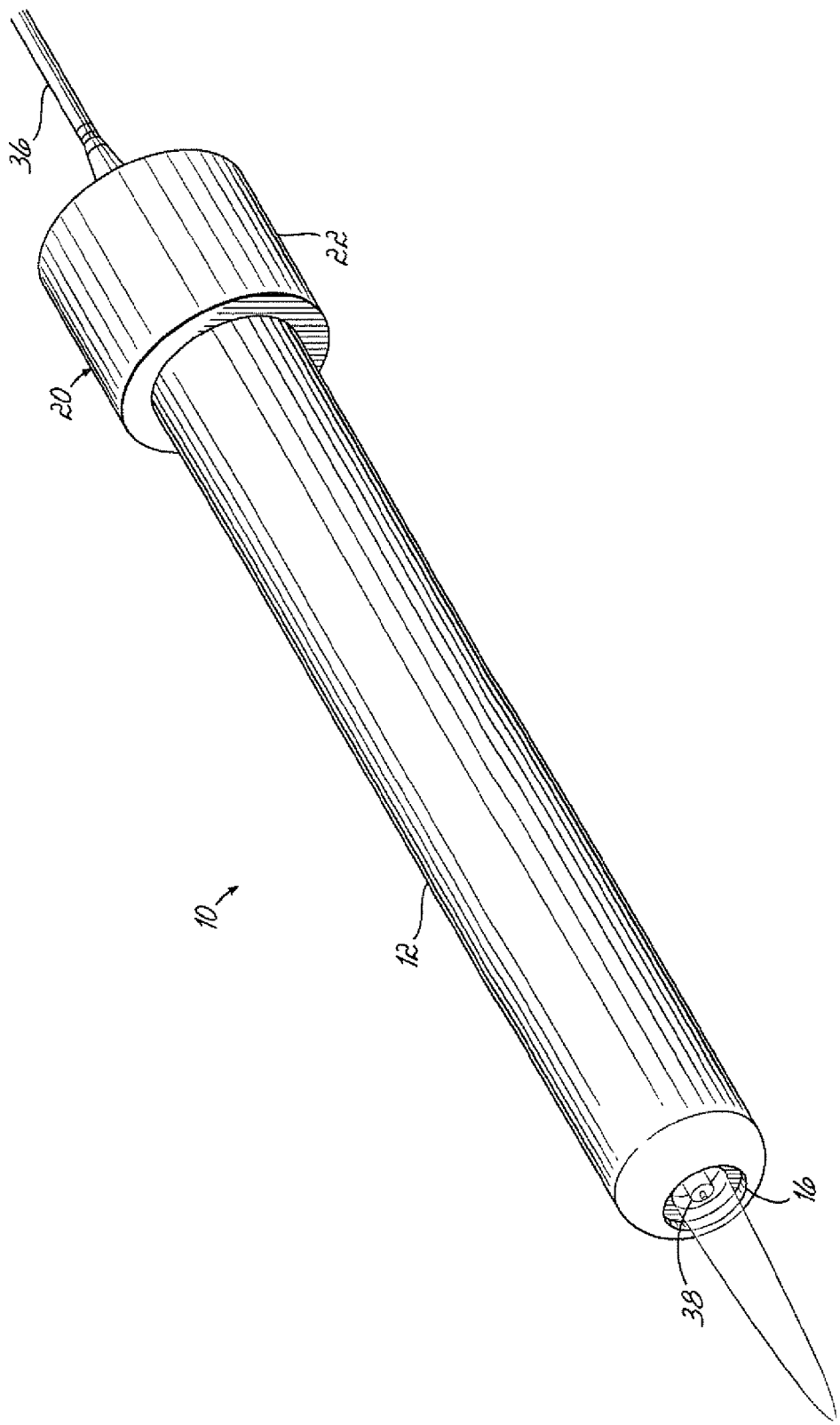
FIG. 1 is a perspective view of an exemplary embodiment of an industrial heating system according to this invention.

Referring to FIGS. 1-3, an exemplary embodiment of an industrial gas heater 10 according to this invention is shown. The heater 10 includes a generally right circular cylindrical tubular housing 12 having a gas entry port 14 at a first end of the housing 12 spaced from a gas exit port 16 at an opposite end of the housing 12. The housing 14 may be a monolithic ceramic tube or other material such as a metallic enclosure. However, we have found that the temperature of the gas heated within the assembly is increased anywhere from 25-200° C. when a ceramic housing is utilized.

The gas entry port 14 is proximate an open end 18 of the housing 12 and is selectively closed by an end cap 20 mounted on the open end 18 of the housing 12. The end cap 20 may be made from a ceramic of approximately 90 percent aluminum oxide. The cap 20 includes an annular sidewall 22 and an end wall 24. The end cap 20 is a partially open end cap and according to various embodiments of this invention, the end cap 20 can be fully or partially open with additional openings for electrical feed-throughs and thermocouple feed-throughs. A stepped passage 26 is formed on the interior of the sidewall 22 and the gas entry port 14 is on the end wall 24. The opening diameter of the gas entry port 14 to the gas exit port 16 may be at a ratio of about 2:1.

The gas heater 10 includes an inner helical coil 28 and an outer helical coil 30 contained within the tubular housing 12. The inner and outer coils 28, 30 are coaxially aligned and concentrically arranged as right circular helical coils within the housing 12 to define a substantially unobstructed annular space 32 for passage of gas through the housing 12 from the gas entry port 14 to the gas exit port 16. In one embodiment, each coil 28, 30 is formed from a generally continuous wire 28a, 30a, respectively, concentrically wound into right circular helical coils. A diameter of the wire 28a, 30a for each coil may range from about 0.1 mm to about 6 mm. A gap 28b, 30b between the adjacent turns 28c, 30c of each coil 28, 30 may range from about 0.01 mm to about 85 mm. The gap or pitch of each coil 28, 30 may increase adjacent to the entry port 14 and terminal lead wires 28d, 30d.

Figure 10:
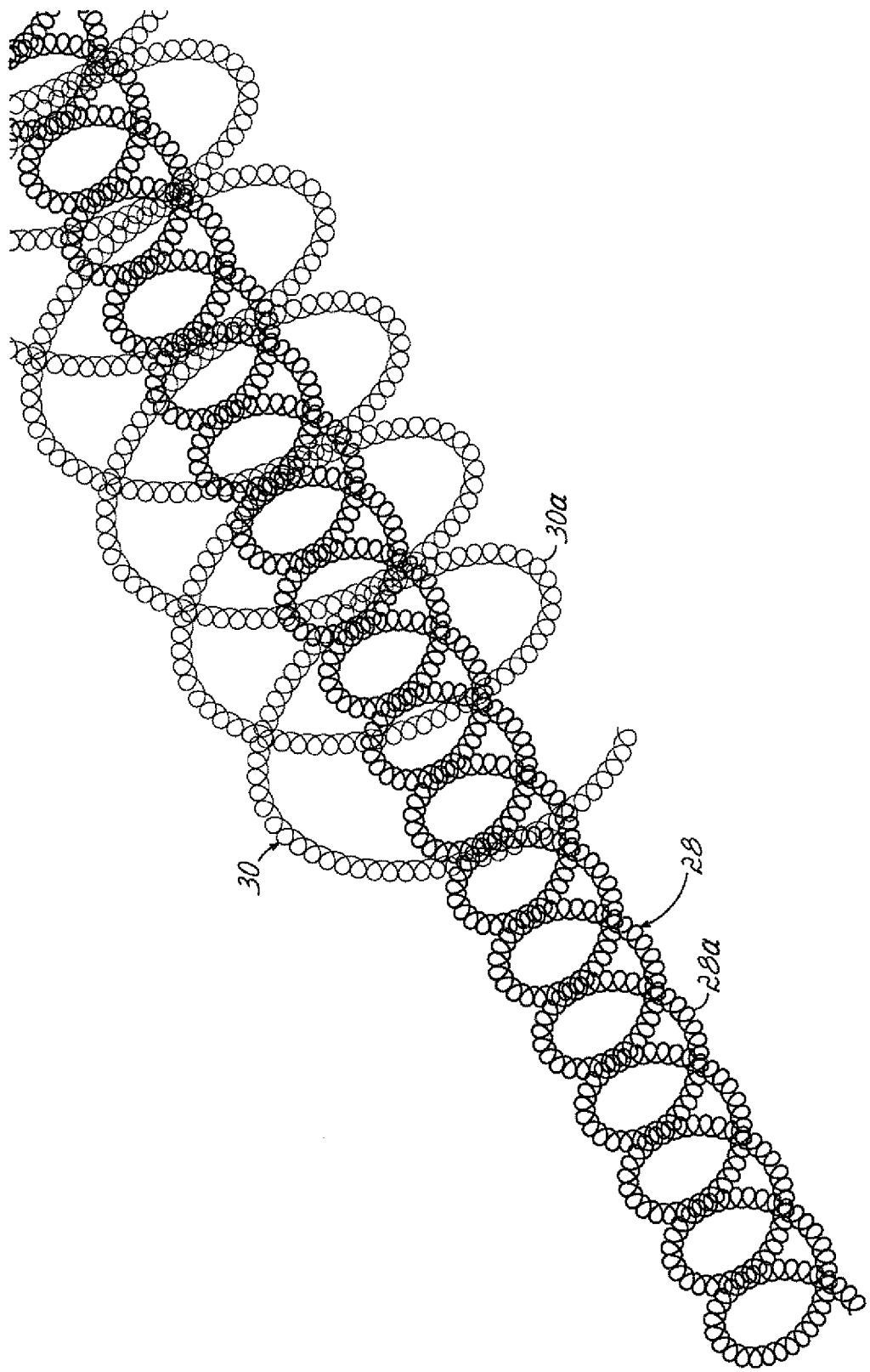
FIG. 10 is a perspective view of an alternative embodiment of heating coils to be utilized in an industrial heating system according to this invention.

In a further embodiment as shown in FIG. 10, the wires 28a, 30a of either or both of the coils 28, 30 are themselves right circular helical coils to increase the heat transfer from the coils 28, 30 to the gas. The diameter of the coiled-coil configuration of FIG. 10 may range from about 0.5 mm to about 10 mm. At least a portion of the inner coil 28 may include a cover or sheath (not shown) concentrically disposed about the inner coil 28. In one embodiment, the cover may be an adherent thin-film coating, such as a ceramic paste or other suitable material. In another embodiment, the cover may include a sleeve that slides over the coil. The sleeve may be a continuous tube or be formed from a plurality of short tubular section (e.g., 1 mm long alumina tubes). In any event, the cover is adapted to be electrically non-conductive but capable of transmitting heat efficiently. Accordingly, those of ordinary skill in the art may recognize other arrangements and configurations of the cover in accordance with aspects of the invention. It should be recognized that only a portion of the inner coil 28 may include the cover. Alternatively, substantially the entire inner coil may include the cover. Moreover, the at least a portion of the outer coil 30 may also include a cover as described above. The cover(s) may protect the coils 28, 30 and extend the useful life of the heater.

We have found that where the outer coil 30 is in close proximity to and/or in contact with the inside face of the tubular housing 12, the gas processed in the heater 10 is heated approximately 25° to 200° C. higher than if the outer coil 30 is not in such a configuration relative to the housing 12. Additionally, a spacer 34 which may be ceramic is positioned at the distal end of the coils 28, 30 proximate the gas exit port 16. The spacer 34 increases the useful life of the coils 28, 30 and minimizes coil deformation over extended periods of use.

Figure 4:
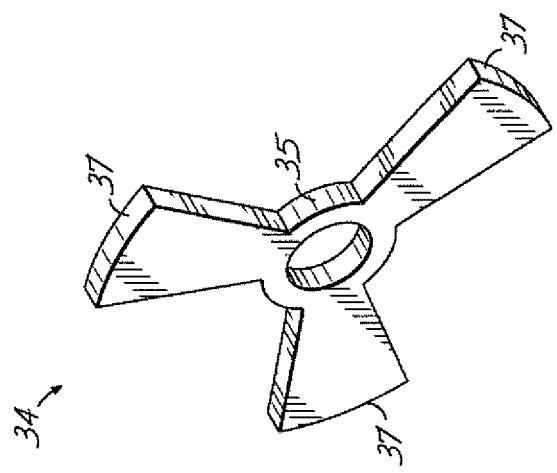
FIG. 4 is an enlarged perspective view of a spacer utilized in the heating systems of FIG. 1.

One embodiment of the spacer 34 is shown in FIG. 4 and includes a central, annular circular ring 35 that is adapted to be mounted on a central rod 40. The rod 40 may be ceramic or another material. The spacer 34 has a number, three of which are shown in FIG. 4, vanes 37 radiating outwardly from the ring 35. The vanes 37 are equally spaced around the circumference of the ring 35 and each have an outwardly tapered or flared configuration.

Terminal lead wires 28d, 30d extend from the proximal end of the respective coils 28, 30 and through the end wall 24 of the end cap 20 to be electrically coupled to a power cord 36 and a power source (not shown) for heating the coils 28, 30. Any power requirement may be appropriate for the coils 28, 30, but typically 110-volt (approximately 1 kilowatt) modules are utilized. Other voltages, including 220-240 volt, 30 volt, 60 volt, and others depending on the application, in either a modular construction of a single construction are contemplated to be within the scope of the invention.

A thermocouple lead 38 is positioned coaxially and longitudinally within the coils 28, 30 for reading the gas temperature adjacent the gas exit port 16. The thermocouple 38 is mounted on the central rod 40 positioned coaxially relative to the inner and outer coils 28, 30 in the housing 12. The arrangement and juxtaposition of the coils, thermocouple, central rod and housing are among the features of the present invention that provide for a very compact, space-saving design for the gas heater.

Figure 5:
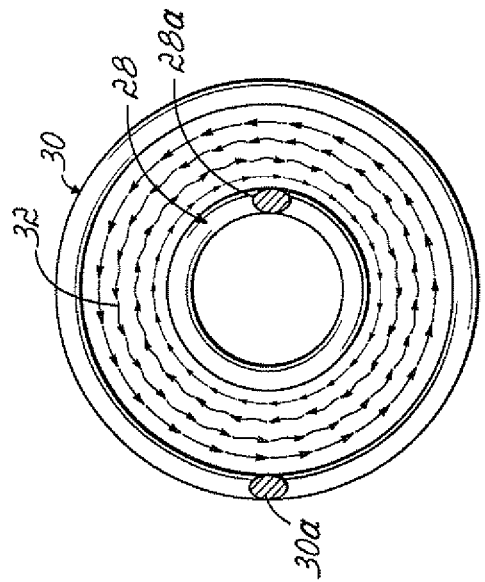
FIG. 5 is a cross-sectional view showing an annular space between inner and outer heating coils of the system of FIGS. 1-3.
Figure 6:
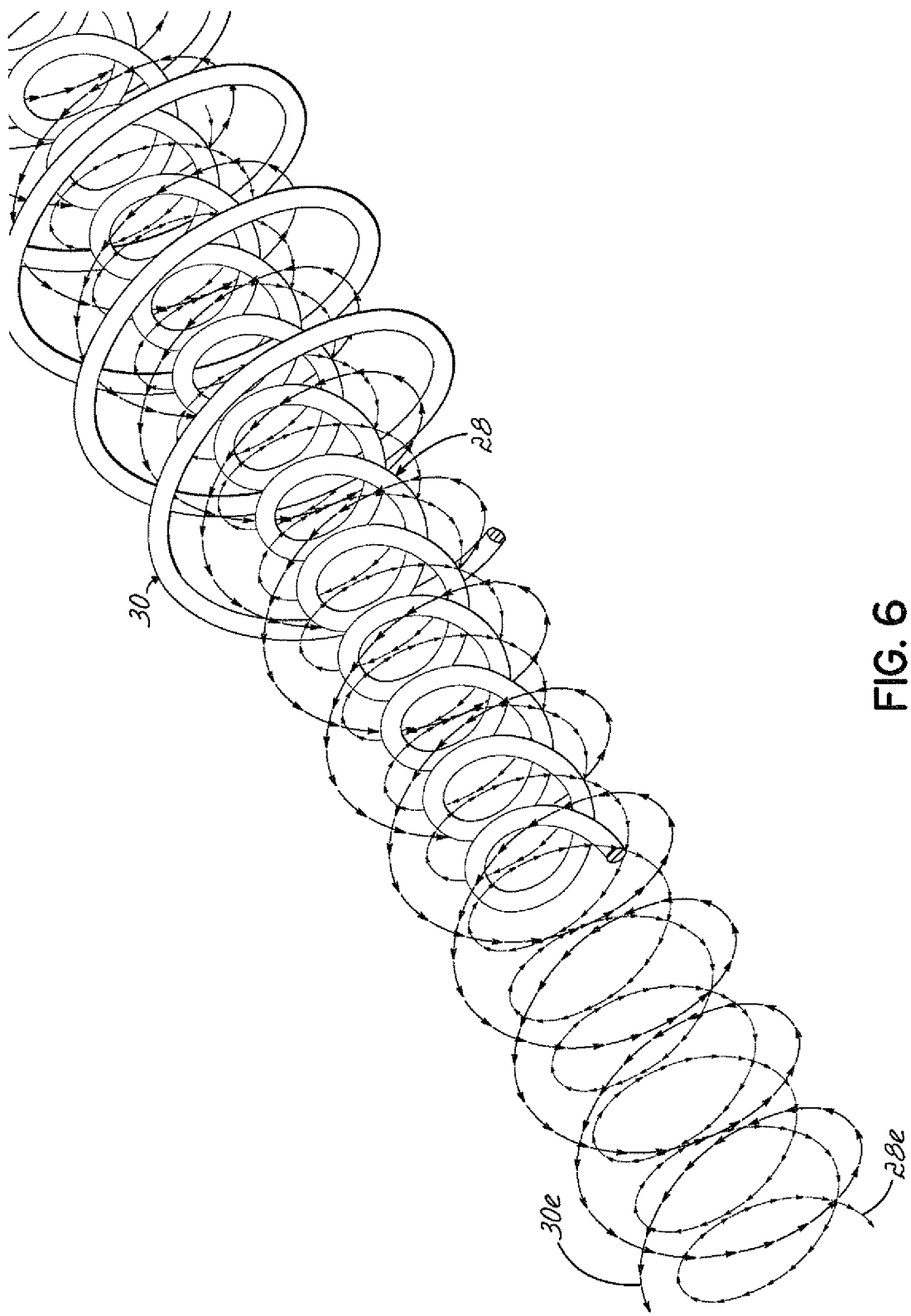
FIG. 6 is a perspective schematic view of the rifling airflow through the inner and outer heating coils.

Among the advantages provided by a gas heater 10 according to this invention is the increased contact between the gas flowing from the entry port 14 to the exit port 16 with the coils 28, 30. For example, the coils 28, 30 may be similarly wound or wound in opposite directions as shown in FIG. 6. Gas flowing through the housing 12 passes through the annular space 32 between the coils 28, 30 as shown in FIG. 5. The annular space 32 and flow path of the gas in this area is generally unobstructed to provide for appropriate thermal exchange from the coils 28, 30 to the gas. Additionally, gas flowing between the adjacent turns 28c, 30c of the respective coils 28, 30 flows in a riffling or spiraling configuration as schematically shown in FIG. 6 with flow paths 28e, 30e. With the windings of the respective coils 28, 30 being in opposite direction, increased mixing of the gas with the coils 28, 30 is provided to obtain a more turbulent gas flow. The thermal exchange may be further enhanced with the coil 28, 30 configuration shown in FIG. 10. Each of these arrangements provides for increased thermal transfer from the heated coils 28, 30 to the gas relative to prior art industrial gas heating systems.

Radial dimensions of the annular spacing 32 (FIG. 5) may range from about 1.5 mm to about 20 mm with a presently preferred annular spacing 32 being about 2 mm. The range of gap spacing between the adjacent turns 28e, 30c of the wires 28a, 30a in the coils 28, 30 is between about 35 mm and about 85 mm with the presently preferred being about 40 mm for the inner coil 28 and about 65 mm for the outer coil 30. The cross sectional area of the annular spacing 32 ranges between about 15 mm$^2$ to about 6000 mm$^2$ with the presently preferred being derived from the above-identified gap spacing ranges.

Figure 8:
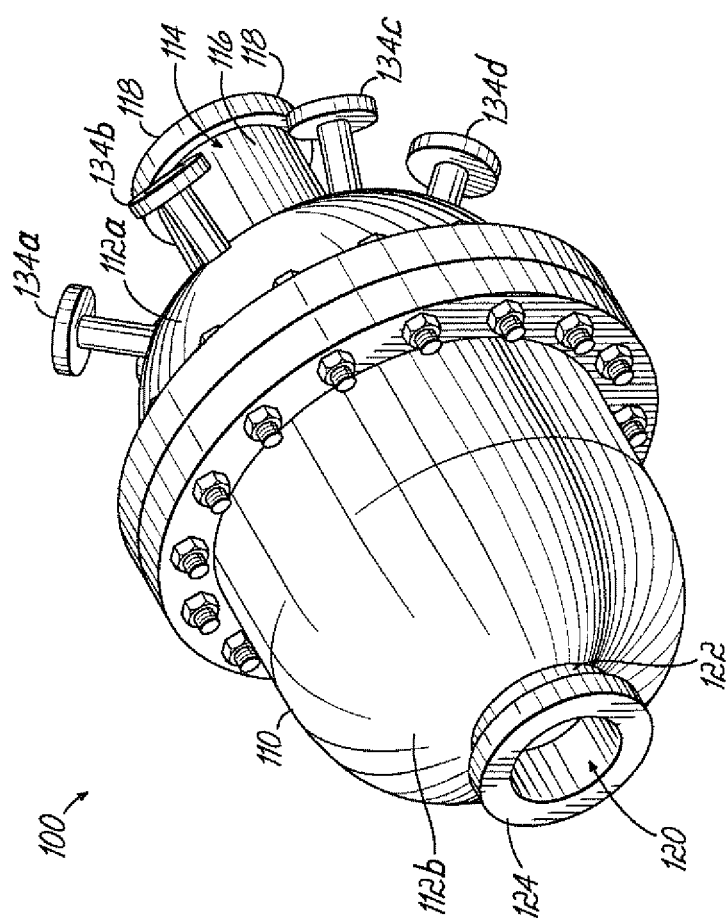
FIG. 8 is a perspective view of a further embodiment of an industrial heating system according to this invention.
Figure 9:
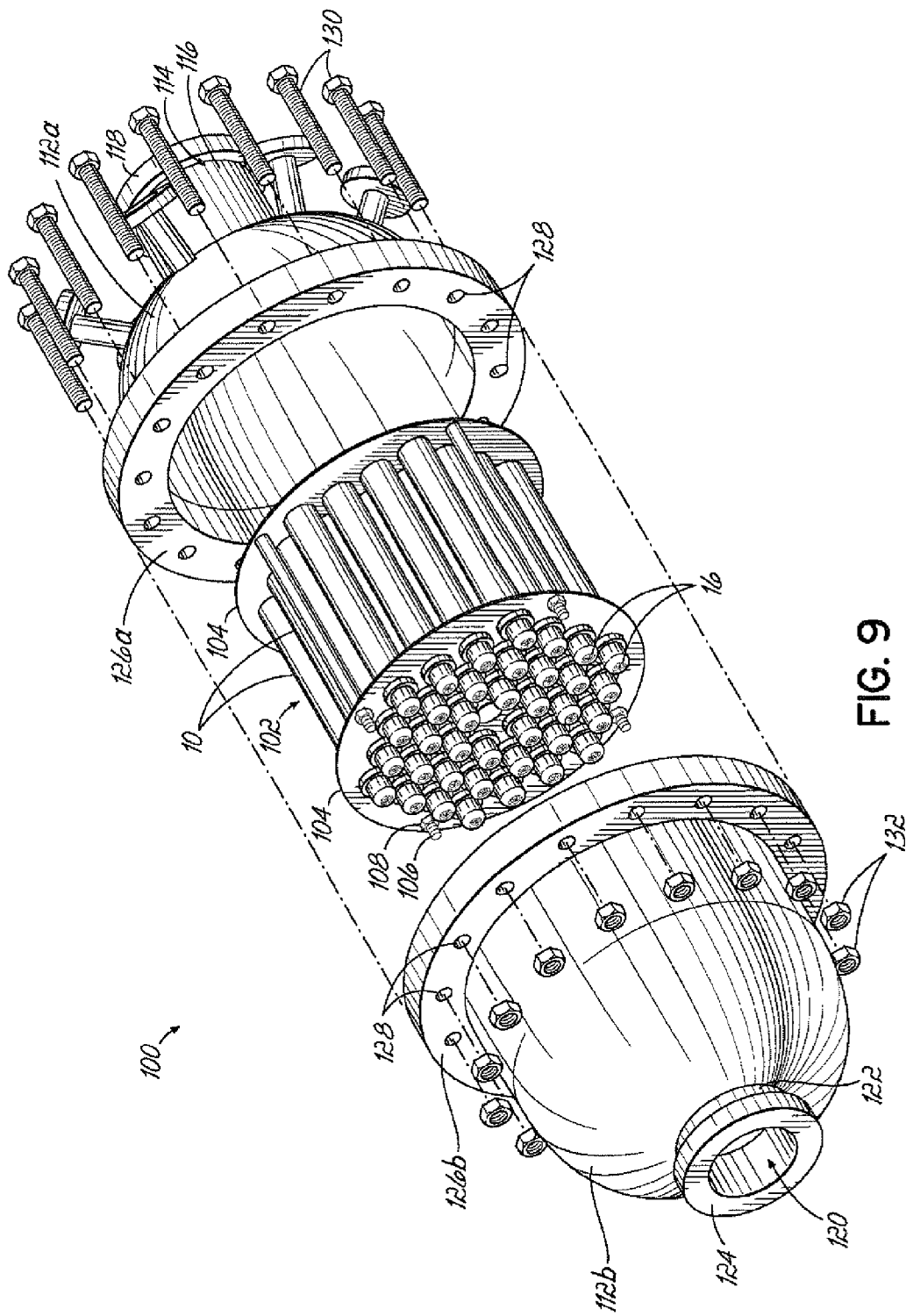
FIG. 9 is a partially disassembled perspective view of the system of FIG. 8.

An alternative embodiment of an industrial heating assembly 100 according to this invention is shown in FIGS. 8-9 with components of the heating assembly 100 that are the same or similar to corresponding components of the heater 10 being labeled in a similar manner. The heating assembly 100 according to this embodiment of the invention utilizes a heating cartridge 102 with multiple gas heaters 10 of the type disclosed in FIGS. 1-3 mounted in a generally parallel orientation relative to each other between a pair of generally circular spaced end plates 104. The end plates 104 are maintained in a spaced configuration by a series of spaced threaded rods or bolts 106 positioned around the periphery of the plates 104 and secured to the plates 104 by mechanical fasteners such as nuts 108 or the like. The cartridge 102 is shown in one configuration and those of ordinary skill in the art will readily appreciate that the number of gas heaters 10, their arrangement and configuration is available in a wide variety of different embodiments according to this invention.

The cartridge 102 is mounted within a sealed chamber 110 which is formed by a pair of mating dome-shaped enclosures 112a, 112b. The enclosure 112a proximate a gas entry port 114 of the heating assembly 100 includes a gas entry conduit 116 having a flange 118 adapted to mate with a gas feed supply (not shown). The enclosure 112b at a gas exit port 120 of the heating assembly 100 likewise includes a conduit 122 and compatible flange 124 for mating with downstream equipment to provide a sealed heating assembly 100.

Each of the dome-shaped enclosures 112a, 112b includes a peripheral flange 126a, 126b which is adapted to mate with the corresponding flange of the other enclosure 112a, 112b as shown in FIG. 9. The flanges 126a, 126b each include a number of through holes 128 which, when aligned with a corresponding through hole in the opposite flange, allow a threaded bolt 130 to pass therethrough so that a nut 132 can be threadably mounted on the bolt 130 to secure the flanges 126a, 126b and dome-shaped enclosures 112a, 112b together to provide the sealed chamber 110. A gasket or other seal (not shown) may be provided and sandwiched between the flanges 126a, 126b as appropriate. The appropriate valves, gauges and instrumentation 134 may be mounted in communication with the interior of the chamber 110 for monitoring the gas heating therein. Various embodiments of the industrial gas heating assembly 100 shown in FIGS. 8-9 may be provided in 12 kW, 24 kW and 36 kW, 48 kW, 60 kW or other designs having various combinations of power and fluids.

Figure 7:
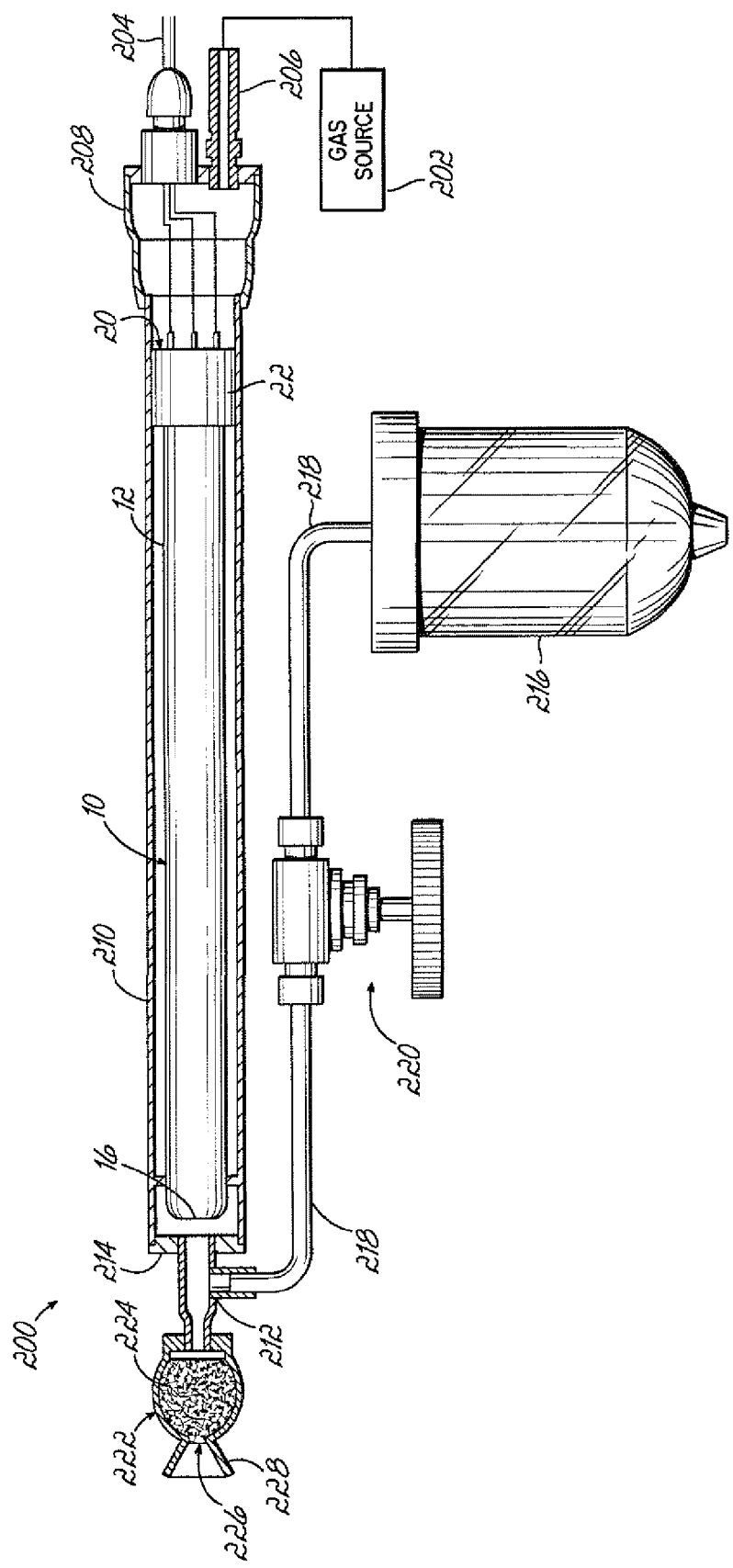
FIG. 7 is a perspective view of another embodiment of an industrial heating system according to this invention adapted to convert liquid to high temperature gas, e.g., generate supersaturated steam.

A further embodiment of an industrial heater 10 according to this invention is shown in FIG. 7 and is adapted to generate superheated steam. Traditionally, boiling water at high pressure and then heating the steam at high pressure have produced superheated steam. The embodiment of FIG. 7 provides a device where the flow of hot air over an orifice causes a super saturated steam jet. Components of the industrial heater and steam generator 200 shown in FIG. 7 that are the same or similar to corresponding components of the heater 10 as shown in FIGS. 1-5 are labeled in a similar manner. The words "superheated", "supersaturated" and variations thereof are interchangeable. Superheated steam for the purposes of this specification is steam at less than 100° C. at 1 atmosphere or at high pressures greater than 1 atmosphere. It also encompasses $H_2O$ in the form of gas at any temperature. Although we use the word steam to illustrate making $H_2O$ gas or vapor we anticipate with this word any embodiment for the conversion of any fluid to a gaseous state with our apparatus and method. The word supersaturated steam is used to indicate $H_2O$ or other materials in the form of gas at temperatures above 100° C. at pressures of about 1 atmosphere (see FIG. 7) and/or higher (see FIG. 9). By supersaturated steam we also infer $H_2O$ in the form of vapor. One objective of this aspect of this invention is to make supersaturated steam at 1 atmosphere; whereas, it normally takes high pressure to make supersaturated steam. Although we use the word steam to illustrate making $H_2O$ gas or vapor we anticipate with this word any embodiment for the conversion of any fluid to a gaseous state with our apparatus and method. We also intend to use the words superheated and supersaturated interchangeably.

The heater and steam generator 200 includes a gas inlet source 202, which may be pressurized or unpressurized, and a power cord grip 204 proximate a gas inlet 206 of the device. A manifold housing 208 is mounted on the gas entry end of a casing 210 that is generally a right circular tube. An industrial gas heater 10 according to a variety of embodiments according to this invention such as those shown in FIGS. 1-3 is mounted within the casing 210.

Proximate the gas exit port 16 of the industrial gas heater 10, a delivery tube 212 is mounted to an end plate 214 of the casing 210. The delivery tube 212 is in communication with a fluid reservoir or cup 216 which may be a polycarbonate reservoir for housing a working fluid, such as water. The delivery tube 212 advantageously includes a venturi assembly therein. A supply or feed line 218 from the reservoir 216 is regulated by a needle valve 220, the operation of which is well know by those of ordinary skill in the art. The valve 220 may be either mechanical, electromechanical, semiconductor, nano valve, needle valve, self regulation condition by water level or any other commonly understood regulating device with or without feedback. The feed line 218 is coupled to the delivery tube 212 as shown in FIG. 7. The supply feed line 218 may be stainless steel piping or other appropriate material. The delivery tube 212 feeds into a reactor vessel 222 having a generally bulbous configuration. Contained within the reactor vessel 222 is a porous medium 224 such as steel wool or other generally non-dissolvable media; however, a dissolvable media may be utilized within the reactor vessel 222, if appropriate. The porous medium 224 may be made of metallic, ceramic, polymer, intermetallic, nano-materials, or composite materials or combinations and mixtures thereof. The porosity may be reticulated or well defined. The porosity may be even or uneven and may vary from nanometer-size to centimeter sized pores. An exit nozzle 226 is provided on the reactor vessel 222 and may include a diffuser 228.

The liquid to be heated into super saturated steam is contained within the reservoir 216 and fed to the venturi tube through the inlet pipe as regulated by the needle valve. The gas heated by the gas heater passes into the delivery or venturi tube 212 that is connected to the fluid reservoir 216. As the hot gas passes through the venturi tube 212, it draws the liquid from the reservoir 216. The liquid flow as previously stated is controlled by the needle valve 220. The liquid is atomized in the venturi tube 212 and the liquid/gas mixture enters the reactor vessel 222 where the liquid is vaporized. The unique design of the reactor vessel 222 provides for total vaporization of the liquid. The vaporized fluid exiting the reactor vessel 222 may be re-circulated through the system 200 and introduced into the gas inlet 206. Furthermore, the apparatus and method of this invention may produce steam by the addition of $H_2O$ through one or both of the coils in the gas heater 10. This introduction of the $H_2O$ may be at the inlet, outlet or in-between the gas passage and the $H_2O$ may be added in the form of a liquid, gas or mist. In addition, the $H_2O$ may be in combination with other fluids and/or particulates, including nano-molecules, silver nano-particles, and other suitable particles. For example, sol-gel type of nano-molecules may be used in embodiments of the invention.

We have noted that the position of the valve 220 influences the air steam mixture. For example, at 100 ml of water in 462 seconds, a high 40% specific humidity value at 375° C. at about 1.3 CFM of hot air is generated. The relative humidity is estimated to be about 40% at this temperature assuming full compositional scale ideal gas mixing with no mixing enthalpy. Further, at 375° C., a pressure of 22 MPa (i.e., approximately 220 times atmospheric pressure) is needed to initiate condensation of the mixture. Alternatively, cooling the gas to about 110° C. at one atmosphere is required to initiate condensation. Specific humidity is defined as the mass of $H_2O$ divided by the mass of air.

Steam temperature depends on the water valve 220 setting and air inflow setting. Typical settings at a full power of 1 kW for the gas heater 10 are as follows: gas at 1.45 CFM and water at 200 ml in 45 minutes yields steam air temperature of approximately 350° C. Gas at 1.4 CFM and water at 200 ml in 20 minutes yields steam air temperature of about 250° C. Further, gas at 1.8 CFM and water at 200 ml in 20 minutes yields steam air temperature of about 150° C. The above examples utilize a gas inlet temperature at approximately 30° C. and the water inlet temperature at approximately 30° C. Other combinations of power, energy and flow may be used for each fluid and combinations thereof.

Possible applications for the industrial heating assembly and steam super saturated generator 200 of FIG. 7 include high temperature superheated steam-air or steam-gas generation. This could be utilized for layering, epoxy drying and other film uses where superheated steam is required at one atmospheric pressure. Applications for formica polymeric materials, drying, degreasing, wood conditioners etc. are contemplated. This application is ideal for steam drying or steam oxidation as well as for spray deposition and spray cooling. Nano-crystal and larger crystal-sized production is possible by dissolving, gasification (i.e., steaming) and precipitation on cooling the gas. Silicon purification may be possible also for use in thermo-electrics and solar cell applications. Other applications for the system of FIG. 7 include fogging, gas moisturizing, hot coating, steam generation, vapor deposition, cooking, rice making, cleaning, drying and epoxy hardening. Applications in energy devices such as fuel cells are anticipated. As discussed more fully below, heater and seam generator 200 may also be used in microorganism management.

The following graph provides exemplary data of how to adjust the system 200 of FIG. 7 for different levels of specific humidity. Note as the specific humidity increases, there is a corresponding decrease in overall temperature as total energy is conserved. For the following graph, the steam gas thermocouple is positioned at the gas exit port. Variations of the data shown in the following graph may be expected to be varied upon replacement of the thermocouple, restrictions on gas and water flow and other random errors normally present in multi-variant measurements. As one of ordinary skill in the art will appreciate, specific applications would require optimization of all valve settings for optimum results. Standard water steam temperature, pressure diagrams and saturated steam and superheated steam pressure and temperature tables may be utilized for such optimization.

Various embodiments of the heaters 10, 100, 200 according to this invention were tested and the results are summarized and presented herein. The following tests were done with (1) metallic wire and (2) with molybdenum disilicide wire and the following results were obtained.

Metallic Wire.

Commonly available metallic heating wire 28a, 30a made of Nickel Chromium alloy or Fe—Al—Cr or Fe—Al, Ni—Cr alloy was used. Generally, such metallic wires can be heated in air to about 1200° C. Wire diameters from 0.1 mm to a 1.2 mm were tried for the experiments. We conducted the following experiments with the Fe—Al—Cr alloy. Alloys made of Fe—Al—Cr—Nb or Fe—Al—Cr—Mo—Nb were expected to perform similarly as are other metallic and intermetallic systems.

In one experiment, the gas was heated to 850° C. at a 3.5 SCFM (standard cubic feet per minute, standard conditions are normally 25° C. and 1.0 atmosphere) flow rate with the following design features of the heater. Other experiments were also conducted where gas was heated to close to 1000° C. The experiment utilized a wire coil with a wire diameter of 1.2 mm for the inner and outer coils 28, 30. The outer coil wire 30a separation (pitch) was 0.285 mm and the inner coil wire 28a separation (pitch) was 0.285 mm. The wires 28a, 30a of the inner and outer coils 28, 30 were wound in opposite directions. A thermocouple 38 was located at about 3 mm from the gas exit port 16. When located at this location, the thermocouple read up to 980° C. It is expected that the upper range with metallic elements will be about 1000° C. for ambient air. Other gases, depending on their thermal properties, will have a different exit temperature. Metallic elements made of Mo, W or other such higher temperature metals provide higher gas exit temperatures up to 3000° C.

We contemplate that the wire sizes for the inner and outer coils 28, 30 could be different for different industrial applications. Similarly the pitch can be different for each coil 28, 30 and different at different locations in the same coil according to this invention. For example, the coil pitch proximate to the incoming power leads 28d, 30d could be larger than at the main heating sections of the coils 28, to keep the contacts relatively cooler. Spacers and other inserts between the coils 28, are contemplated, if required, according to this invention.

It is thought that the presence of the inner coil 28 serves to overcome the surface or conda effect and thus improves contact with the gas flowing through the tubular housing 12.

Some further experiments were conducted. Coil design was adjusted with the appropriate physics in mind.

Experiment 1

The outer coil 30 provides rifling of the gas that increases heat transfer from the coil to the gas. A helical coil wire 30a of 240 mm long and 13.2 mm mean diameter, working out for 8.2 Ohms (18SWG A1 commercial wire) was used for testing. The coil was inserted in an open-ended ceramic tube 12. The exit end of the coil was brought back to the inlet side through a ceramic insulating tube. The coil was operated at 110V, at a power rating of 1.47 kW. The airflow was maintained at 5 SCFM at 0.4 Kgs/cm$^2$ working pressure. The exit temperature of the air stabilized at 560° C.

Experiment 2

The inner coil 28 overcomes the conda surface effect, and provides for annular area heating of the gas, which provides for the highest heat transfer to the gas. The exit end of the coil 28 was wound on its return on the ceramic insulating tubular housing 12. The resulting coil resistance was 10.8 Ohms. The coil 28 was operated with the same airflow, air pressure and operating voltage of 110V as in Experiment 1. The coil now operated at 1.1 kW, and the exit temperature stabilized at 806° C.

Experiment 3

The inner coil 28 was wound in the opposite direction of the outer coil 30 to provide opposite rifling to the gas with respect to the outer coil. This causes a turbulence effect on the airflow, which increases heat transfer to the gas. All other parameters were the same as Experiment 2. The exit temperature stabilized at 845° C. Therefore, the opposite winding configuration gave a nearly 50° C. higher temperature. Table 1 below gives further experimental details and exit temperatures.

Experiment 4

An experiment was conducted with an inner coiled-coil 28 and an outer coiled-coil 30 (FIG. 10). The gap was between 6 to 10 min (i.e. the outer diameter (OD) of the inner coiled-coil, was 40 mm and the inner diameter (ID) of the outer coiled-coil was about 60 mm). The wire 28a, 30a itself was 0.8 mm in diameter and the diameter of the coiled-coil was about 8 mm. The material of the wire was Fe—Cr—Al alloy. At about 1.6 SCFM we found a temperature of 650° C. was reached in a few minutes at the exit for air. When water was introduced as a mist, at the inlet point a final steam gas temperature of 230° C. was obtained.

Experiment 5

Several modules as described in Experiments 3 and 4 were arranged in parallel and superheated steam was generated both by mist injection before the coil and ahead of the coil. This air-supersaturated steam was continuously recirculated through the assembly in order to increase the H$_2$O content in the gas. Experiments are continuing in order to get more quantitative readings of the specific humidity. The modules and method of heating were found to be suitable for recirculation.

TABLE 1

| Experiment Number | Coil resistance (Ohms) | Voltage (Volts) | Current (Amps) | Airflow cross section area (mm2) | Power (kW) | Air Flow (SCFM) | Air Pressure (Kg/cm$^2$) | Exit temperature of air (° C.) |
|---|---|---|---|---|---|---|---|---|
| Experiment 1 | 8.2 | 110 | 13.4 | 25.1 | 1.47 | 5 | 7 | 560 |
| Experiment 2 | 10.8 | 110 | 10 | 17.2 | 1.1 | 5 | 7 | 806 |
| Experiment 3 | 10.8 | 110 | 10 | 17.2 | 1.1 | 5 | 7 | 845 |
| Experiment 4 | 11.0 | 110 | 10 | 55.2 | 1.1 | 3.5 | 0.4 | 850 |

TABLE 2

Typical Results of the Present Invention

| Time | Temperature, C. Set point | Temperature, C. Process | Flow, SCFM | Secondary Current | Secondary Volts | Primary Current | Primary Volts | Comments |
|---|---|---|---|---|---|---|---|---|
| 10:00 | 0 | RT | 2.0 | 0 | 0 | 0 | 0 | Started |
| 10:03 | 1400 | 542 | 2.0 | 93 | 14 | 16 | | |
| 10:05 | 1400 | 1167 | 2.0 | 103 | 21 | 18 | | |
| 10:07 | 1400 | 1371 | 2.0 | 95 | 21 | 18 | | |
| 10:08 | 1400 | 1400 | 2.0 | 106 | 18 | 15 | | |
| 10:20 | 1400 | 1402 | 2.0 | 105 | 18 | 18 | | |
| 10:30 | 1400 | 1400 | 2.0 | 79 | 16 | 14 | | |
| 10:38 | 1400 | 1400 | 2.0 | 77 | 16 | 13 | | |
| 10:38:50 | 1400 | 1400 | 3.0 | 86 | 18 | 14 | | |
| 10:48 | 1400 | 1400 | 3.0 | 86 | 17 | 14 | | |
| 10:58 | 1400 | 1400 | 3.0 | 81 | 16 | 14 | | |
| 11:08 | 1400 | 1400 | 3.0 | 81 | 16 | 15 | | |
| 11:08:50 | 1400 | 1400 | 4.0 | 89 | 18 | 16 | 81 | |
| 11:20 | 1400 | 1400 | 4.0 | 96 | 19 | 17 | | End |

UAT5 Ref: p83(4)
HIPAN Primary: 208 Volts,
Secondary: 40 Volts tap.
RT: Room temperature

TABLE 3

Typical Results of the Present Invention

| Time | Temperature, C. Set point | Temperature, C. Process | Temperature, C. In-situ | Flow, SCFM | Secondary Current | Secondary Volts | Primary Current | Primary Volts | Comments |
|---|---|---|---|---|---|---|---|---|---|
| 9:35 | 0 | RT | RT | 3.0 | 0 | 0 | 0 | 0 | Started |
| 9:39 | 1050 | 1046 | 621 | 3.0 | 89 | 13 | 15 | | |
| 9:42 | 1372 | 1334 | 942 | 3.0 | 102 | 19.6 | 18 | | |
| 9:43 | 1372 | 1372 | 1032 | 3.0 | 95 | 18.5 | 17 | | |
| 9:47 | 1372 | 1372 | 1055 | 3.0 | 123 | 22 | 19 | | End |
| 10:47 | 1400 | 392 | 432 | 3.0 | 0 | 0 | 0 | 0 | Re-started |
| 10:49 | 1400 | 1042 | 702 | 3.0 | 124 | 19.7 | 22 | | |
| 10:50 | 1400 | 1375 | 954 | 3.0 | 98 | 18.8 | 17 | | |
| 10:51 | 3400 | 1397 | 1022 | 3.0 | 95 | | 16 | | |
| 10:52 | 1400 | 1400 | 1074 | 3.0 | 89 | 17 | 16 | | |
| 11:00 | 1400 | 1400 | 1165 | 3.0 | 81 | | 15 | | |
| 11:10 | 1500 | 1500 | 1279 | 1.0 | 70 | | 12 | | |
| 11:13 | 1500 | 1500 | 1301 | 1.0 | 67 | 14 | 12 | 81 | |
| 11:18 | 1500 | 1500 | 1314 | 1.0 | 66 | 12 | 12 | | |
| 11:26 | 1500 | 1500 | 1316 | 0.5 | 56 | 11 | 10 | | |
| 11:28 | 1500 | 1500 | 1315 | 1.0 | 60 | 12 | 10 | | |
| 11:39 | 1500 | 1500 | 1316 | 1.0 | 58 | 11 | 10 | 88 | |
| 11:53 | 1500 | 1500 | 1322 | 1.0 | 57 | 11 | 10 | 69 | |
| 12:05 | 1500 | 1500 | 1322 | 1.0 | 56 | 11 | 10 | 69 | |
| 12:55 | 1500 | 1500 | 1324 | 1.0 | 55 | 11 | 10 | | |
| 1:31 | 1500 | 1500 | 1324 | 1.0 | 55 | 11 | 10 | | |
| 2:05 | 1500 | 1500 | 1328 | 1.0 | 55 | 11 | 10 | | |
| 3:30 | 1500 | 1500 | 1332 | 1.0 | 55 | 11 | 10 | | |
| 5:00 | 1500 | 1500 | 1332 | 1.0 | 55 | 11 | 10 | 70 | End |

UAT5 Ref: p95(4)
HIPAN Primary: 240 Volts,
Secondary: 40 Volts tap.

It is contemplated that molybdenum disilicide wires 28a, 30a can be heated in air to 1900° C. for this invention. However, such wires are more brittle than metallic wire. The molybdenum disilicide coils were obtained from Micropyretics Heaters International, Inc. of Cincinnati, Ohio (www.MHI-INC.COM).

Wire 28a 30a diameters of 3 mm, 4 mm or 5 mm may be used with this invention. An experiment was conducted with outer coil wire 30a separation (pitch) at 12.7 mm and inner coil wire 28a separation (pitch) at 12.7 mm. The gap between the coils 28, 30 tested was varied from 4 mm to 15 mm. Best results were obtained with the 5 mm wire.

The best test results of Table 2 show a temperature of 1165° C. to 1400° C. at different measurement positions with 1400° C. as set point on the controller and airflow set to 1 SCFM.

The best test results of Table 3 show a temperature of 1332° C. to 1500° C. at different measurement positions with 1500° C. as set point on the controller and airflow set to 1 SCFM. In an experiment with the inner coil 28 at about 40 mm and the outer coil at about 65 mm, a wire thickness of about 0.8 mm and coil of about 1 mm diameter Fe—Cr—Al alloy, barely separated for the coiled wire embodiment, the exit temperature with air was 650° C. with a flow rate of about 1.6 SCFM (estimated approximate). The pitch separation of the coils may be smaller for metallic coil materials and larger for ceramic materials. We were also able to introduce a water mist into these coil arrangements and obtain a high quality steam output (see FIG. 7).

As a result of this invention, as yet unavailable very high temperatures in gases for industrial applications are obtainable because of the new coil in coil design with the proper spacing and gaps with the two coils 28, 30 electrically coupled. It is also found that opposite winding in the inner and outer coils 28, 30 gives rise to very high temperatures of the gas at the exit port 16.

The typical industrial applications for this invention involve low cost heating. Three different types of industrial applications are considered without limiting the invention from other industrial applications:

1. Heating of any gas, including steam, directed into chamber such as an oven or furnace that may or may not have other heating systems in it.
2. Heating of any gas, including steam, passing though the coils.
3. Heating any gas, including steam, directed at a surface for applications such as coatings, hardening, debinding, glowing, etc.

The coils 28, 30 may be electrically heated or heated by a combination of electric and other thermal methods. The coils 28, 30 can be metallic, molybdenum disilicide, silicon carbide, intermetallic, ceramic or other materials.

Another application for a heater and steam generator, such as that shown in FIG. 7, for example, is in the field of microorganism management. There are many industries interested in either the reduction or elimination of bacteria, viruses, fungi, spores, and other pathogenic microorganisms. For example, the food industry, medical industry, waste management industry, agriculture industry, public health concerns, and many others have a vested interest in the reduction or elimination of such unwanted microorganisms. The ability to sterilize, disinfect, or otherwise treat various items for microorganisms in a quick, convenient, and cost effective manner has caught the public's attention due to the increased number of cases involving the so-called superbug, or antibiotic resistant microorganisms. By way of example, schools, day care centers, hospitals, nursing homes, vacation destinations, cruise ships, and many other private and public places may be susceptible to outbreaks involving various microorganisms, including the superbug. Such outbreaks typically require the facility to be closed and thoroughly cleaned so as to reduce or eliminate the likelihood of further infections. These outbreaks are major disruptions to these facilities or businesses, are costly to address, and may harm the reputations of the facilities or businesses (e.g., hospitals, restaurants, and other businesses) in which such outbreaks occur through negative publicity. Moreover, in future space travel, the ability to destroy possible new strains of microorganisms discovered in other atmospheres and bodies may be facilitated by embodiments in accordance with the invention.

The typical manner in which these industries manage microorganisms, not only during such an outbreak, but also as prophylactic measures, is to use various chemicals or other cleaning agents that reduce of eliminate microorganisms. For example, some common cleaning agents include chlorine (e.g., Clorox, Purex); stabilized chlorine dioxide (e.g., Oxyfresh Dent-A-Gene); phenols (e.g., Lysol); chlorhexidine gluconates (e.g., Nolvasan, Phisohex, Virosan, Hibitane); quaternary ammonium compounds (e.g., Roccal-D, Quintacide, Parvosol, Hitor, Merquat, and Cetylcide); Glutaraldehydes (e.g., Wavecide, Cidex, Sporcide, Banacide, and Sterol); alcohols; iodines (e.g., Vanodine, Betadyne, Povidone, Scubodyne); and pine oil (e.g., Pine-Sol and Hexol). In this regard, the various items to be cleaned or disinfected, including cooking or food preparation surfaces, desks, door knobs, railings, showers, sinks, toilets, water fountains, and other common area items, are wiped or scrubbed with these cleaning agents to reduce or eliminate microorganisms and the threat of microorganism infestation. Although generally successful for its intended purpose, chemical sterilization or disinfection, such as that described above, may be costly and may be associated with negative effects on the environment and individuals that come into contact with the chemicals.

The use of supersaturated steam for various other purposes is generally known. For example, a wide variety of steam-generating apparatus (e.g., steamers) are commercially available for such applications. Such steamers, however, have a number of drawbacks that limit their use. For example, steamers typically generate supersaturated steam by increasing the pressure within a sealed chamber containing saturated steam from a boiler. Because pressure is used, steamers effectively operate as pressure vessels that result in relatively heavy, bulky designs which may be difficult to use and maneuver. Additionally, steamers typically require large boilers for steam generation. In this regard, because steamers operate at increased pressures, a significant amount of steam has to be generated to reach saturated conditions inside the chamber at the elevated, superheated temperatures. The amount of steam required at the increased pressures mandates that relatively large boilers be utilized. These boilers are typically included with the steamers, which adds significant weight and size to the steamer.

In addition, steamers typically require a relatively large amount of steam because mixing of the steam with the surrounding environmental fluid (e.g., air) typically occurs external to the steamer. In this regard, the pressure-generated supersaturated steam is released from the steamer, such as through a nozzle or operatively connected hand piece, and mixes with the surrounding air to provide a steam-air mixture that cleans, disinfects, etc. It is believed, however, that the concentration of the steam for effectively managing microorganisms may be at a value less than that resulting from simply expelling the superheated steam from the steamer and mixing it with environmental air external of the steamer. However, because substantially pure steam or a steam/air mixture with a relatively high concentration of steam exits the steamer and passively mixes with air outside of the steamer, a large amount of steam must be generated. Accordingly, a large part of the steam, and the energy required to make that extra steam, from the steamer may, in essence, be wasted as that required to reduce or eliminate microorganisms may be achieved with significantly less steam. Due to the manner in which steamers generate supersaturated steam, steamers are generally not able to capitalize on using the steam in a more efficient manner.

Figure 11:
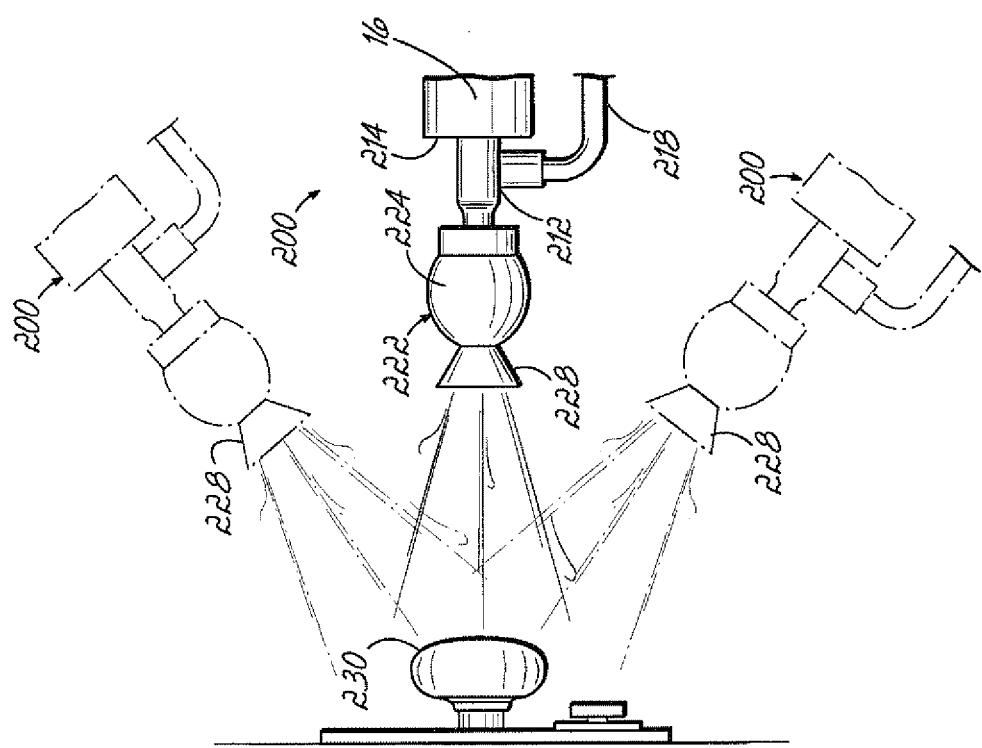
FIG. 11 is a perspective view illustrating use of the apparatus shown in FIG. 7 for reducing or eliminating unwanted microorganisms on an item.

With this in mind, and in another aspect in accordance with embodiments of the invention, the heater and steam generator 200 shown in FIG. 7 and described above may be used to reduce or eliminate unwanted microorganisms which overcomes many of the drawbacks of current methods and devices. As illustrated in FIG. 11, the heater and steam generator 200 may be operated so as to generate a superheated vapor-gas mixture in the manner as described above. In one embodiment, air may be the gas passed through heater 10 and water may be the working fluid in reservoir 216 such that the heater and steam generator 200 produces a superheated steam-air mixture exiting from exit nozzle 228. Other gases and working fluids, however, may also be used in accordance with the invention. The steam-air mixture exiting the assembly 200 may be directed onto an item 230, illustrated as a doorknob in FIG. 11, to be sterilized, disinfected, or otherwise treated to reduce or eliminate unwanted microorganisms associated with the item 230. The superheated steam-air mixture flows onto the item 230 for a time sufficient to reduce or eliminate the microorganisms thereon.

The treatment time may depend on several application-specific factors, including the size, shape, penetration of steam into the item, power of the heater, distance between the apparatus and item 230, thermal properties of the item 230, etc. It is contemplated, however, that a treatment time of between just a few seconds to about sixty second would be sufficient in most cases. Those of ordinary skill in the art will recognize how to determine the amount of time to treat an item to effectuate reducing or elimination microorganisms on a particular item. The treatment time may also depend on the temperature of the superheated steam-gas mixture exiting the apparatus. While for industrial gas applications as described above, the operation temperature range was between about 500° C. and about 1,500° C., for microorganism applications an operational temperature range may be between about the saturation temperature of the working fluid and about 1,500° C. For example, with steam, the lower bound of the operational temperature range is about 100° C. Moreover, the specific temperature may depend on the capability of the item 230 to withstand higher temperatures. Those of ordinary skill in the art will recognize how to set or determine the operational temperature of the apparatus. It is contemplated that treatment using heater and steam generator 200 may be effective for a wide range of microorganisms including without limitation *listeria monocytogenas, escherichia coli, pseudomonas aeruginosa, salmonella typhimurium, salmonella enteritidis, delegionella bacteria, staphylococcus aereus* (resistant drain), *bacillus subtilis, enterobacter aerogenes, streptococcus faecalis, legionella pneumophila, viibrio parahaemolyticus, bacillus cereus*, and other gram positive and gram negative microorganisms. It is further believed that viruses such as hepatitis may also be destroyed using heater and steam generator 200. Furthermore, it is believed that aspects in accordance with embodiments of the invention may also be effective for reducing the spread of tubercolosis and related AIDS.

There is virtually no limit to the various items 230 that may be sterilized, disinfected or otherwise treated using the heater and steam generator 200 as described above to reduce or eliminate unwanted microorganisms associated (e.g., on or in) the item. For example, and without limitation, many household items may be treated, including kitchen sinks, countertops, tables and appliances; bathroom items such as sinks, toilets, showers, etc.; other common area items including door knobs, handrails, televisions, remotes, etc. Many common area items in public facilities such as schools, libraries, day care centers, grocery stores, retail stores, shopping malls, hospitals, nursing homes, etc. may also be treated with the heater and steam generator 200 to reduce or eliminate unwanted microorganisms. For example, various medical instruments may be cleaned or sterilized with heater and steam generator 200, including endoscopes, tubes (thin and thick), and other hard to clean, intricate medical and non-medical devices. In this regard, such instruments may be oriented adjacent and substantially parallel to the outlet of the heater and steam generator 200 such that superheated steam may flow though the interior of the item (e.g., through a lumen of the item). The food industry, including, restaurants, cafeterias, meat packaging plants, slaughter houses, other food process facilities, animal farms (e.g., poultry farms) and devices associated therewith (e.g., various animal holding devices), may also benefit by treating items associated therewith using superheated steam or other superheated fluids generated by the heater and steam generator 200. In general, the heater and steam generator 200 may be used to sterilize, disinfect, or otherwise treat items for which the chemical agents identified above are normally used. Those of ordinary skill in the art will recognize a host of other items which may be treated with the heater and steam generator 200.

The use of heater and steam generator 200 to reduce or eliminate unwanted microorganisms overcomes many of the drawbacks of existing devices and methods. By way of example, in one embodiment, the heater and steam generator 200 may not use any chemical cleaning agents, such as those provided above as well as others known in the art. Instead, only water may be used as the working fluid to effectuate reducing or eliminating microorganisms. The invention is not so limited, however, as in other embodiments, various chemical agents may be used with the heater and steam generator 200 to supplement the sterilization or disinfecting process provided by the superheated steam. For example, the cleaning agents provided above or others known in the art may be mixed with the water in the fluid reservoir 216. Other liquids may also be used including paracetic acid, alcohol, chlorine formaldehyde, propylene oxide, hydrogen peroxide, glutavaldehyde, pesticides, and sodium compounds like benzanates. Various wound healing fluids, like non-alcohol based Dermacyn®, may be used with the apparatus, either alone or in combination with other fluids, such as water. In this regard, such non-alcohol fluids will not ignite, even when used at very high temperatures. Although chemical agents may be used in this embodiment, it is believed that a significantly less amount of the chemical agent need be used in such a sterilization or disinfecting process as compared to conventional chemical treatment as described above. In still another embodiment, the fluid reservoir may contain only a liquid chemical, which is vaporized in the reactor vessel 222 to create a superheated vapor-gas mixture that effectuates reducing or eliminating unwanted microorganisms. While in this embodiment, a chemical agent is used as the working fluid, it is again believed that a significantly less amount of the chemical agent need be used in such a sterilization or disinfecting process as compared to conventional chemical treatment.

The use of heater and steam generator 200 to reduce or eliminate microorganisms also overcomes many of the drawbacks with existing steamers. As described above, the heater and steam generator 200 generates superheated steam at substantially one atmosphere of pressure, which is unlike the pressure-induced superheated steam generated by steamers. Thus, bulky boilers and pressure chambers are not required and the heater and steam generator 200 may be relatively compact, light weight, mobile, versatile, easy to handle, etc. The heater and steam generator 200 also uses significantly less steam as compared to conventional steamers and thus the size of the fluid reservoir 216 may be significantly smaller. For example, for most applications it is contemplated that a water flow rate between approximately 1 ml/min and approximately 35 ml/min (for a 1 kW heater) may be sufficient to generate superheated steam to effectuate reducing or eliminating unwanted microorganisms. Moreover, the superheated steam-air mixture that exits the heater and steam generator 200 may include a steam concentration optimized to reduce or eliminate microorganisms. Thus, for example, it is believed that a superheated steam-gas mixture with a steam concentration of no higher than approximately 30% may be sufficient to effectuate microorganism management. Those of ordinary skill in the art will recognize that lower or higher steam concentrations may be used as dictated by the specific application. The heater and steam generator 200 may be configured to provide such a range of concentrations. As described above, for example, the needle valve 220 and/or the flow rate of the gas (e.g., air) through heater 10 may be varied to provide an optimized setting. In this way, the steam may be used in an efficient manner to reduce or eliminate microorganisms. In other words, because the heater and steam generator 200 provides for mixing of the superheated vapor (e.g., steam) with a gas (e.g., air) prior to exiting the apparatus, a more efficient sterilization or disinfecting process may be performed. As noted above, passive mixing of the steam with environmental air is an inefficient use of the superheated steam as microorganism management may be achieved with comparatively less steam. While heater and steam generator 200 may be configured to have a steam concentration of no more than 30% for effectiveness, the heater and steam generator may be able to produce mixtures having a concentration up to about 75% depending on power, operation temperature, and other factors.

Figure 12:
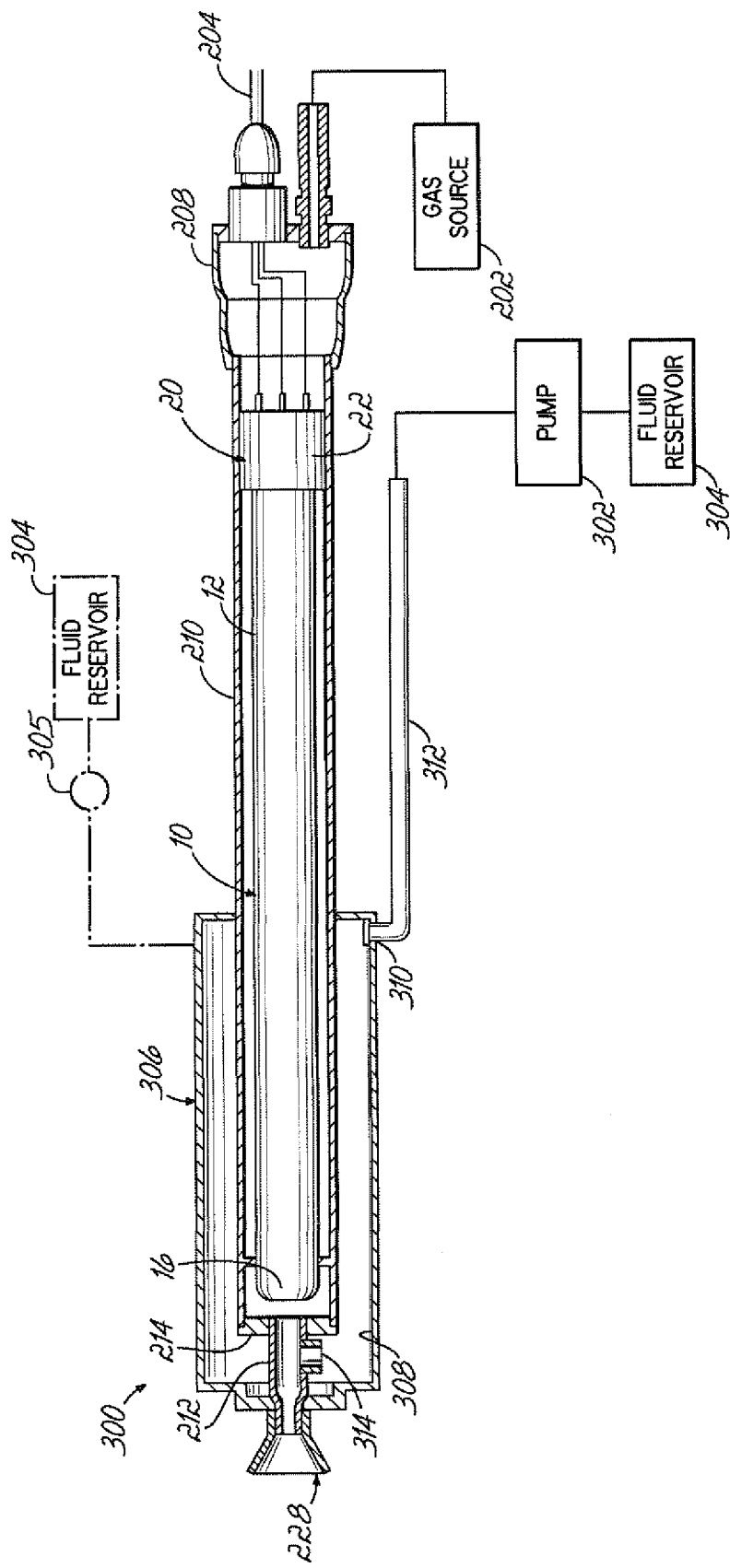
FIG. 12 is a cross-sectional view of a heater and steam generator in accordance with another embodiment of the invention.

A heater and steam generator 300 in accordance with another embodiment of the invention is illustrated in FIG. 12. The heater and steam generator 300 is similar to heater and steam generator 200, and thus only the differences between the two will be described in detail. Similar reference numerals will refer to similar features as shown in FIG. 7. In this embodiment, the use of a venturi to draw the working fluid from fluid reservoir 216, and the use of the reactor vessel 222 may be eliminated. Instead, and in one embodiment, a pump 302 may be used to actively supply the working fluid to the heat and steam generator 300 from a fluid reservoir 304. For example, the pump 302 may be a peristaltic pump having the necessary controls for selectively metering the flow rate of the working fluid (e.g., water) to the heater and steam generator 300. Such peristaltic pumps are commercially available. Other arrangements for supplying the working fluid to the heater and steam generator 300 are also within the scope of the invention. By way of example, a passive arrangement (shown in phantom in FIG. 12) may be utilized wherein the fluid reservoir 304 (e.g., water bag, cartridge, etc.) supplies the working fluid to the heater and steam generator 300 through gravity, for example, or other passive means. In such an embodiment, the reservoir 304 may include appropriate valving 305 (e.g., drip chambers, clips, etc.) for metering the flow of the working fluid to the heater and steam generator 300. Another modification to heat and steam generator 300 is the inclusion of an outer jacket housing 306 that defines a chamber 308 about at least a portion of the casing 210 having an inlet 310 for receiving the working fluid from pump 302 via a suitable conduit 312, and an outlet 314 in fluid communication with delivery tube 212. While the outer jacket housing 306 is shown adjacent the outlet side of the heater and steam generator 300, the housing 306 may be located along other portions of the heater and steam generator.

In operation, the pump 302 or other active or passive supply device supplies the working fluid from the reservoir 304 through conduit 312, through inlet 310, and into the chamber 308 defined by housing 306. The heater 10 heats the casing 210 sufficiently to preheat the working fluid contained in chamber 308 to near or at its saturation temperature (e.g., boiling point). Thus, saturated liquid, saturated vapor or both may be present in chamber 308. Similar to the previous embodiment, the fluid in chamber 308 then flows into the delivery tube 212 where it mixes with the heated gas exiting gas heater 10. The heat from the gas causes the working fluid introduced from chamber 308 to become superheated. In one embodiment, the working fluid is water and the heater and steam generator 300 generates superheated steam. Other working fluids, however, may be used in accordance with aspects of the invention as mentioned above. The end of the delivery tube 212 may include a threaded portion for coupling to various exit nozzles 228 that facilitate directing the superheated vapor-gas mixture (e.g., steam-air mixture) toward various items 230.

The embodiment shown in FIG. 12 and described above may be used in the industrial applications provided above for the embodiment shown in FIG. 7. Moreover, the heater and steam generator 300 may also be used to reduce or eliminate unwanted microorganisms in the manner described above in regard to the heater and steam generator 200 shown in FIG. 7. The heater and steam generator 300 thus provides the same advantages identified above for heater and steam generator 200 in regard to chemical treatment procedures and steamers.

Figure 13A:
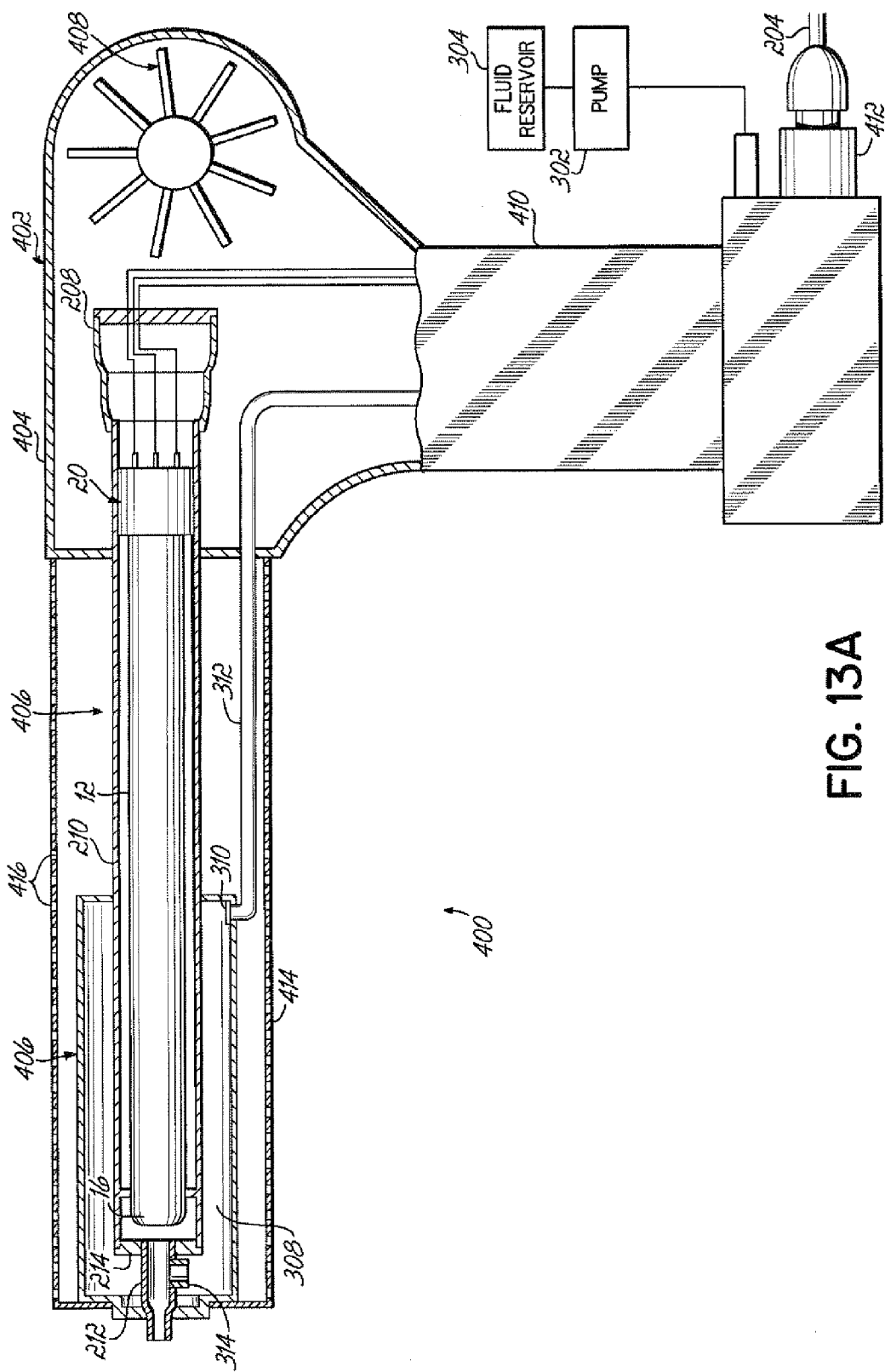
FIG. 13A is a cross-sectional view of a hand-held apparatus in accordance with another embodiment of the invention.
Figure 13B:
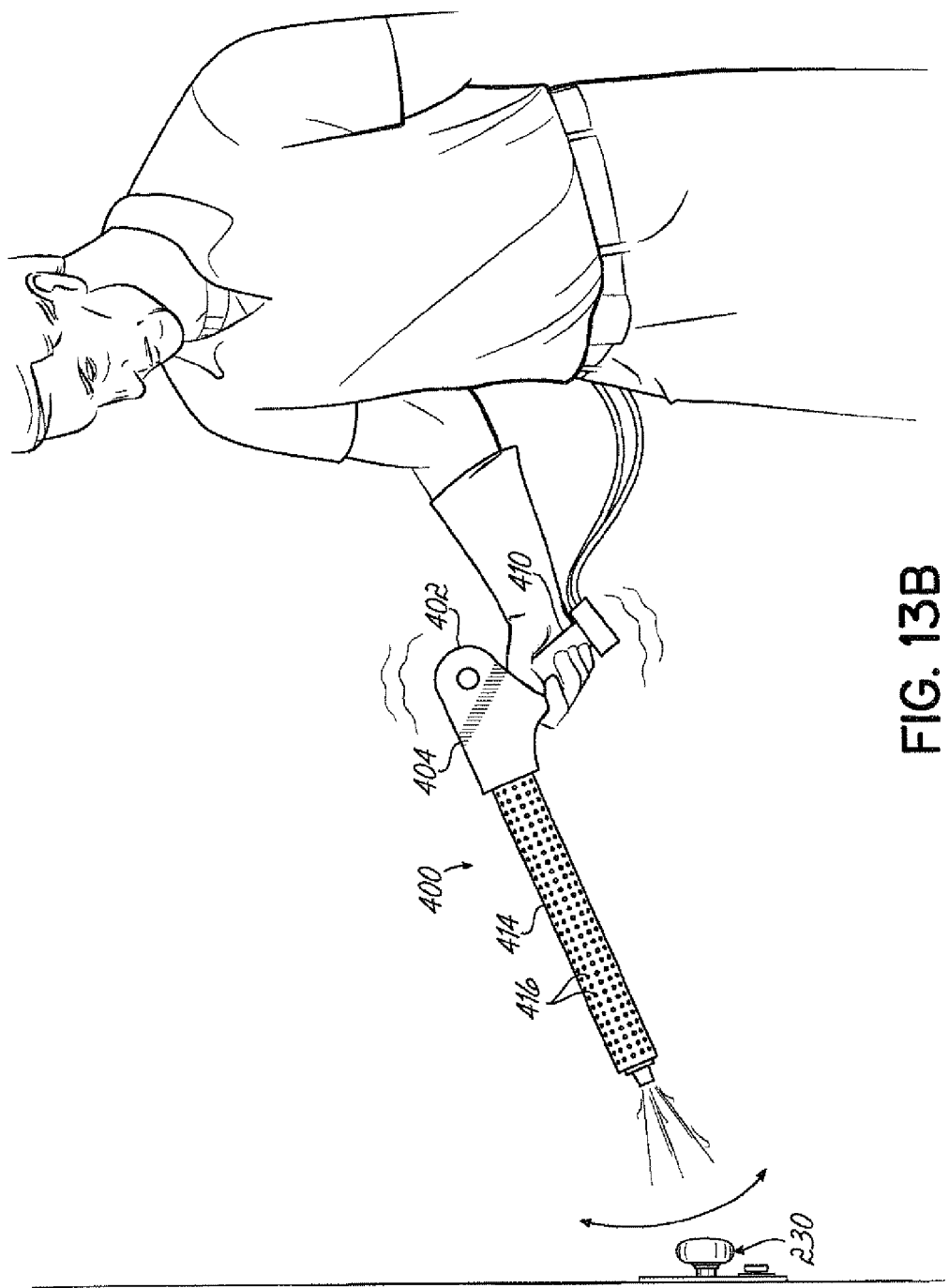
FIG. 13B is a perspective view illustrating use of the hand-held apparatus shown in FIG. 13A in accordance with an embodiment of the invention.

Due to the advantages identified above, a heater and steam generator may be provided in a relatively compact hand-held platform that facilitates the use of such a device in many microorganism management applications. With reference to FIGS. 13A and 13B, a hand-held apparatus 400 adapted to be used to reduce or eliminate unwanted microorganisms on various items 230 includes a housing member 402 having an upper housing portion 404 from which a heater and steam generator 406 projects. The heater and steam generator 406 may be either of the heater and steam generators 200, 300 previously described. For example, as shown in FIG. 13, a heater and steam generator 406 may be configured similar to that shown in FIG. 12, wherein like reference numerals refer to like features. In this embodiment, to make the apparatus 400 more mobile, the gas source 202 may be configured to include a fan 408 in the upper housing portion 404 for supplying environmental air to the heater 10 at a desired flow rate. For example, the housing member 402 may include apertures (FIG. 13B) for providing an access path for environmental air. The fan 408 may include an adjustment knob (not shown) for controlling the flow of air through the heater 10. Other devices recognized by those of ordinary skill in the art may also be used to generate a flow of environmental air through heater 10.

The housing member 402 also includes a handle portion 410 configured to be grasped by a user so as to easily manipulate the apparatus 400 as desired. The housing member 402 may further include various ports 412, such at a lower end thereof, for operatively connecting the apparatus 400 with other devices that facilitate operation of the heater and steam generator 406 or otherwise aid in the operation of the apparatus 400. For example, the housing member 402 may include a port for coupling to a thermocouple for the purposes as described above. Additionally, the housing member 402 may include a port for receiving the working fluid (e.g., water). In one embodiment, for example, a conduit line may be coupled to the port and in fluid communication with pump 302 or other active or passive supply device for supplying the working fluid from fluid reservoir 304 to the heater and steam generator 406. In this embodiment, the pump 302 and reservoir 304 may be remote from heater and steam generator 406 but operatively coupled thereto using suitable conduits. However, in such a hand-held embodiment, the pump 302 and reservoir 304 should remain mobile. Thus, for example, these remote components may be loaded onto a movable cart (not shown) that follows the apparatus 400 and effectively operates as a base for the hand-held apparatus 400. In an alternative embodiment, these remote components may be placed on a backpack (not shown) and configured to be carried by the user during use of the apparatus 400. Those of ordinary skill in the art may recognize other configurations that allow these remote components to be readily moved with the hand-held apparatus 400. Furthermore, while the embodiment shown in FIG. 13A includes a fan 408 for generating air flow through the heater 10, other arrangements are possible. For example, an air compressor or compressed gas source (e.g., pressurized tank) may be mounted on the cart or backpack for supplying the gas to heater 10. In such an embodiment, the housing member 402 may include a port for receiving the gas from such a remote supply.

Power for operating the electrical components of the apparatus 400, such as the heater 10 and the fan 408, may be provided in one of several ways. For example, in one embodiment, the housing member 402 may include a compartment (not shown) for receiving one or more batteries. The batteries may be of the disposable or re-chargeable type and should be configured to provide power to the apparatus 400 for an amount of time corresponding to the specific application. For example, the batteries may last for a shift, day, time period of a particular application or job, etc. In an alternative embodiment, a power source, such as one or more batteries, may be provided with the other remote components, and therefore be on the cart or backpack discussed above. Because the power source is now supported at locations other than the hand-held device itself, more powerful, longer lasting batteries may be used. This may allow the operation times of the apparatus 400 to be extended. In a further embodiment, a motor-powered generator may be carried by the cart or backpack so as to supply power to the apparatus 400. In still a further embodiment, the apparatus 400 may include a power cord 204 which may be coupled to an outlet for supplying the power thereto. Those of ordinary skill in the art may recognize other power sources for providing power to the electrical components of apparatus 400.

To further facilitate use of the hand-held apparatus 400, the heater and steam generator 406 may include an outer tubing or shield 414 surrounding the heater and steam generator 406 extending from the housing member 402. The shield 414 may extend the entire length of the heater and steam generator 406, or only along a portion thereof and is configured to be grasped by a user to manipulate the device. In one embodiment, the shield 414 may include a plurality of vent holes or perforations 416 for providing convective air flow adapted to keep the shield 414 relatively cool. Alternatively, the shield 414 may be made from a material configured to allow a user to grasp the shield 414.

The embodiment shown in FIGS. 13A and 13B and described above may be used in the industrial applications provided above for the embodiment shown in FIG. 7. However, the heater and steam generator 400 may be particularly suited for use to reduce or eliminate unwanted microorganisms in the manner described above in regard to the heater and steam generators 200, 300 shown in FIGS. 7 and 12. The heater and steam generator 400 thus provides the same advantages identified above for heater and steam generators 200, 300 in regard to chemical treatment procedures and steamers.

In still a further application, a heater and steam generator may be used to reduce or eliminate unwanted microorganisms in plant life in agriculture, horticulture, and other soil-based industries. There may also be other benefits to treating plant life with superheated steam. As used herein, plant life generally means any of various photosynthetic, eukaryotic, multicellular organisms of the kingdom plantae characteristically producing embryos, containing chloroplasts, having cellulose cell walls, and lacking the power of locomotion. Embodiments of the invention are directed to treating plant life with superheated steam, or other fluid, and there is virtually no limit on the type of plant life which may be treated. By way of background, one common procedure to manage pests, weeds, and other diseases in various plant life, such as without limitation crops, plants, flowers, trees, shrubs, etc., is to use one or more chemical biocides. These biocides may include, without limitation, methyl bromide 1,3 dichloropropene, metam-sodium, methyl iodide, propargyl bromide, and other chemical agents effective for managing pest, disease, and other attacks by microorganisms. Due to their effect on the environment, and the known and unknown effects on those that consume or handle products treated by the biocides, alternatives are currently being sought. It is believed that one viable and attractive alternative is to treat the plant life with superheated steam or other superheated fluid. Such treatment may reduce or eliminate the microorganisms associated with the plant life or provide other benefits. More particularly, in one embodiment, the soil which supports the plant life may be treated with superheated steam or other superheated fluid for reducing or eliminating unwanted microorganisms therein. The invention, however, is not limited to the treatment of the soil as there may be other treatments with a superheated fluid that provide beneficial. For example, treating the leaves, stems, branches, flower, etc. of plant life may provide a beneficial effect.

In any event, it is believed that such a treatment will improve the quality, e.g., healthier, higher-yielding, plant life (e.g., crops, plants, flowers, trees, shrubs, etc.) without the use of biocides and other chemical agents. By way of example, it is believed that treatment of plant life with a superheated vapor such as steam will improve the height of the plant, the greenness or coloration of the plant, the decay in plant (e.g., number of dead leaves, stems, branches, etc.), the lusciousness of the plant (e.g., the density of healthy leaves, brighter and better flowers, etc.), the susceptibility of the plant life to disease, fungus, and other maladies that afflict plant life, the yield of the plant (e.g., number of flowers, fruit, etc. per plant), and other qualities desirable in plant life. For example, treated plant life may have improved watering requirements as compared to untreated plants. There may also be many more beneficial aspects to treating plant life with a superheated vapor. For example, it is believed that the soil and/or plants thus treated may be less toxic as compared to those treated with various chemicals. Moreover, landfills and other disposal sites, especially where bacterial degradation is not necessarily a factor, which contain soil and/or plants treated in accordance with embodiments of the invention may be healthier to the environment.

Figure 14:
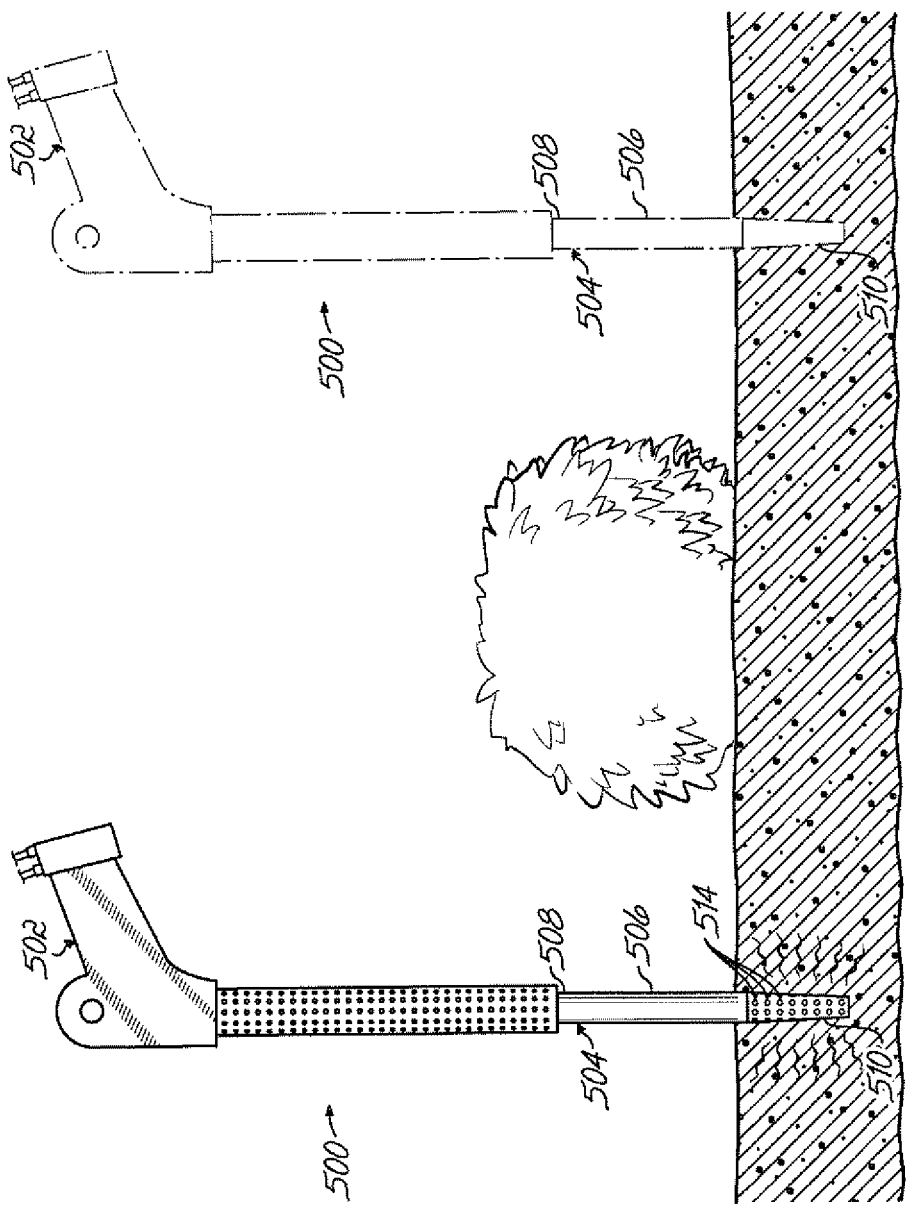
FIG. 14 is a side elevation view illustrating use of the hand-held apparatus shown in FIG. 13A in accordance with another illustrative embodiment of the invention for reducing or eliminating unwanted microorganisms in soil.

An exemplary apparatus 500 for improving the quality of plant life is illustrated in FIG. 14. In one embodiment, the apparatus 500 includes a hand-held heater and steam apparatus 502 similar to that shown in FIG. 13A and described above. The apparatus 500 further includes an adaptor 504 particularly suited for treating the soil in which the plant life is planted with superheated steam. The adaptor 504 includes an elongate tubular body 506 having a proximal end 508, a distal end 510, and a passageway (not shown) extending between the proximal and distal ends 508, 510. The tubular body 506 may be formed from any suitably rigid material including stainless steel, aluminum, iron, other metals, and suitable engineering plastics capable of withstanding the structural requirements of adaptor 504. The proximal end 508 is adapted to be coupled to the outlet of the heater and steam apparatus 502. By way of example, the end of the heater and steam apparatus 502 may include external threads that cooperate with internal threads on the proximal end 508 of the adaptor 504 to effectuate the coupling. Those of ordinary skill in the art will recognize other ways to releasably or fixedly couple the adaptor 504 to the heater and steam apparatus 502. The distal end 510 of the adaptor 504 may be configured to penetrate soil or other growth medium. By way of example, the distal end 510 may be tapered so as to terminate in a relatively sharp or narrow point that eases insertion of the distal end 510 into soil. In addition, the distal end 510 may include one or more holes or apertures 514 therein so as to allow passage of the fluid exiting the heater and steam apparatus 502 (e.g., steam-air mixture) into the soil. The fluid exiting the adaptor 504 is adapted to reduce or eliminate unwanted microorganisms contained in the soil at least in the area adjacent the distal end 510 of the adaptor 504.

In operation, the heater and steam apparatus 502 may be energized so as to generate a superheated vapor-gas mixture exiting therefrom capable of reducing or eliminating unwanted microorganisms. In one embodiment, this fluid may be a steam-air mixture, as explained above. Other liquids may also be used alone or in combination with the steam-air mixture to supplement the sterilization or disinfecting process. For example, liquid plant food, fertilizer and/or other chemical agents may be added to the water or working fluid used for the heater and steam apparatus 502 in the manner described above. The distal end 510 of the adaptor 504 may be inserted into the soil at a first location and the fluid from the heater and steam apparatus 502 may be permitted to flow into the soil. The fluid is permitted to flow into the soil for a specified treatment time sufficient to reduce or eliminate microorganisms. This treatment time depends on the specific application (e.g., kW of heater, distance from item being treated, thermal properties of the surface, and other factors) and may be determined by one of ordinary skill in the art. It is believed, however, that a treatment time of between just a few seconds (e.g., approximately 1 second) to approximately sixty seconds may be sufficient. At the end of the treatment time, the distal end 510 may be removed from the soil. This process may then be repeated at other locations in the soil, as illustrated in phantom in FIG. 14. For example, the soil at several uniformly spaced locations about a planting area for crops, plants, shrubs, trees, flowers, or other plant life may be treated with the superheated steam. The soil may be treated prior to planting in the soil, however, post-planting treatment may also be possible.

Some preliminary tests have been conducted to ascertain the effects of superheated steam on microorganisms in soil. In particular, one soil sample was treated with superheated steam and another control sample was not so treated. After the treatment, both the treated sample and control sample were tested for the presence of bacteria. In this regard, the standard AAMI test procedure was used to test for the presence of bacteria in the samples. As might be expected, testing the samples immediately after the treatment showed a significant decrease in the bacterial count in the treated sample as compared to the control sample. In addition to this result, the preliminary test results further showed that the bacterial count in the treated soil continued to decrease even after the end of the treatment. In this regard, the soil was again tested for the presence of bacteria several hours after the end of the treatment of the soil with superheated steam (e.g., six hours later). Again, a treated sample and a control sample were tested using the standard. AAMI test procedure. Again, the results indicated that the treated sample contained significantly less bacteria than the control sample. Most interestingly, however, was that the bacterial count in the treated sample at the later time period (e.g., several hours later) was less than the bacterial count of the treated sample taken immediately after the superheated steam treatment. These results suggest that treatment with superheated steam or other working fluid may provide some residual benefit above the initial microorganism destruction provided at the time of treatment. Although it is not clearly understood at this time, one theory, without limitation, may be that the superheated steam not only provides the initial kill of microorganisms, but also disrupts the nutrient or food source for the microorganisms, resulting in the additional reduction in bacteria subsequent to the treatment. In any event, what is clear is that treating the soil with superheated steam provided not only an initial decrease in the presence of bacteria, but also provided a residual decrease in bacteria subsequent to the treatment. This may suggest that treating the soil with superheated steam or other working fluid provides a longer-lasting benefit such that the soil, plant life, etc. requires a fewer number of treatments to achieve the desired, positive benefits discussed above.

Figure 15:
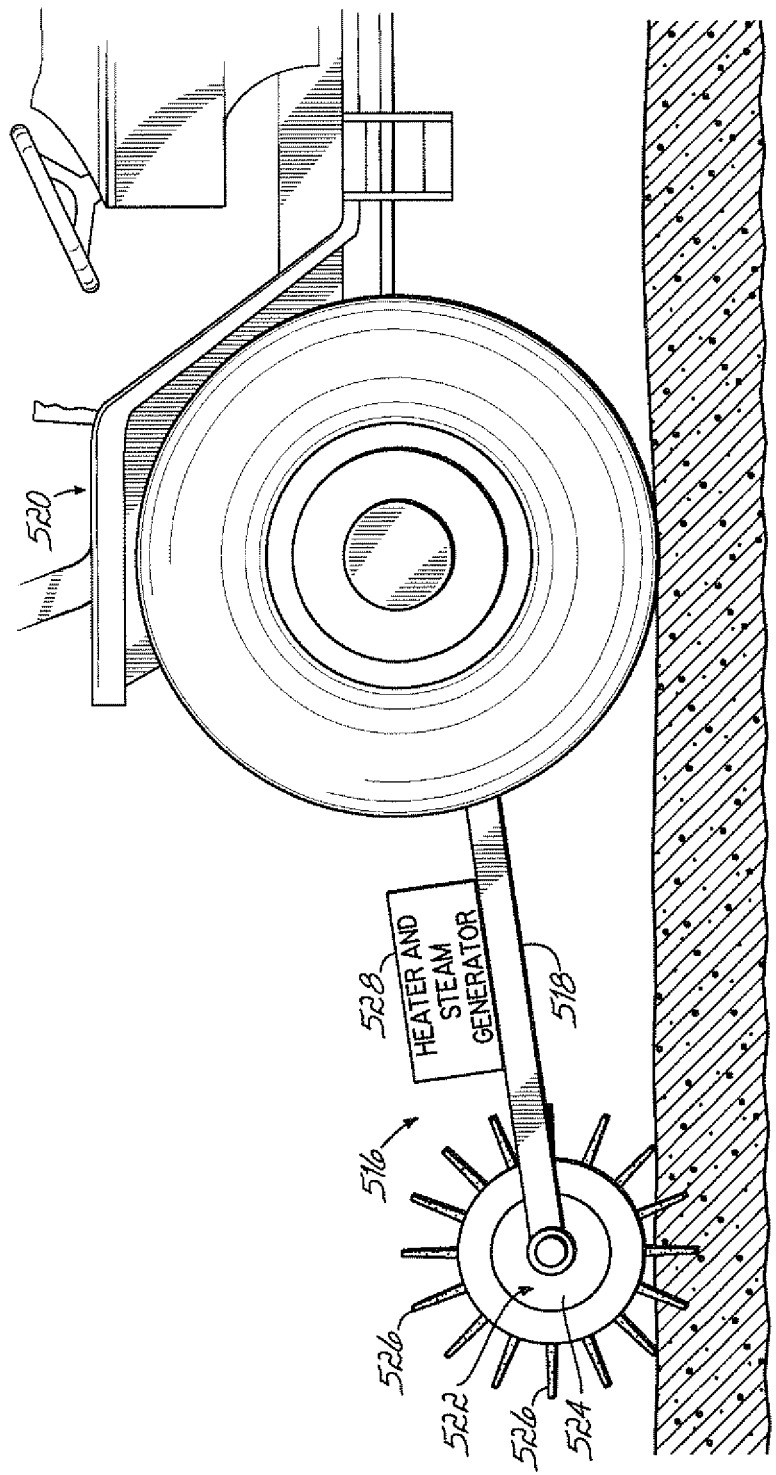
FIG. 15 is a side elevation view of an apparatus for reducing or eliminating unwanted microorganisms in soil in accordance with another embodiment of the invention.
Figure 15:
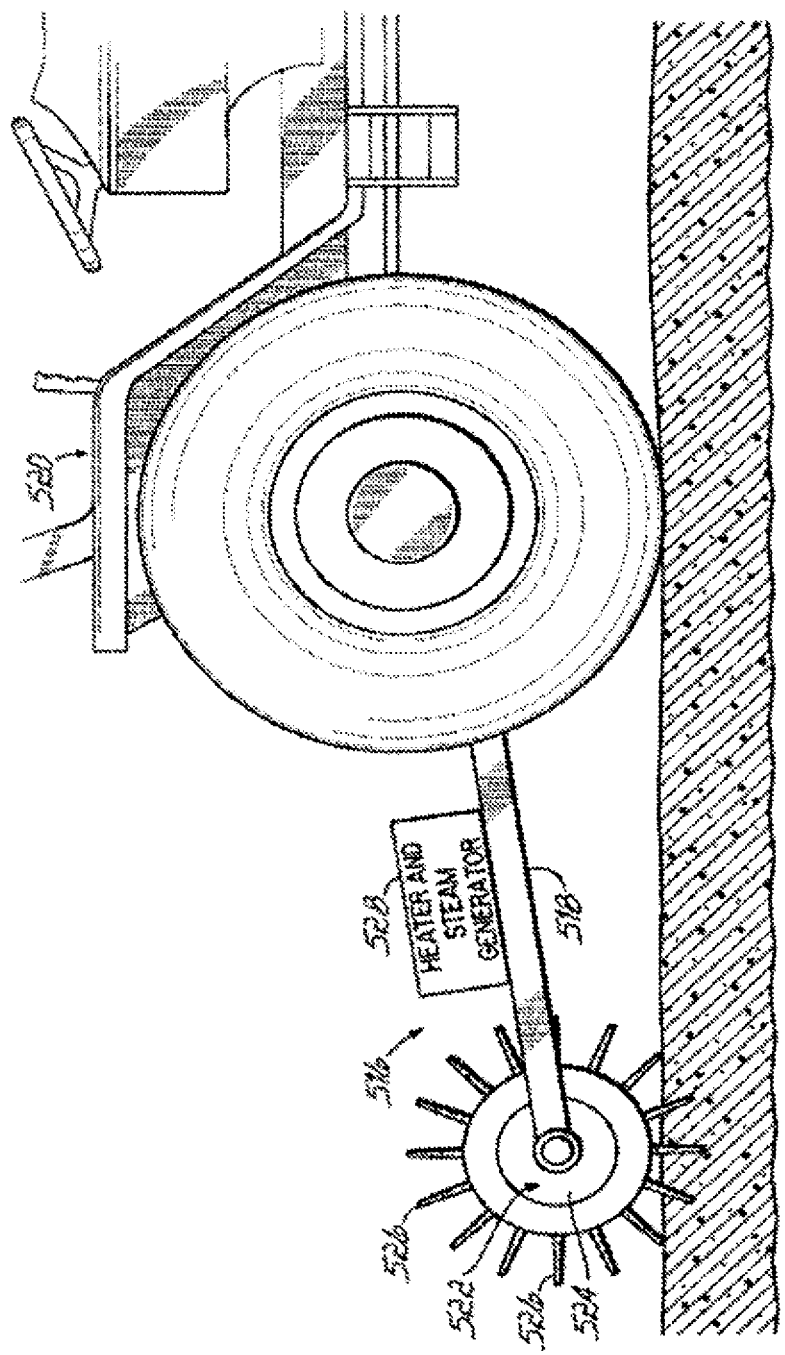

The embodiment shown in FIG. 14 may be particularly suited for small-scale applications, such as for a relatively few number of plants, shrubs, trees, flowers, etc. However, larger scale applications are also possible in accordance with aspects of the invention. By way of example, it is contemplated that a piece of farm equipment for pulling behind a tractor or other vehicle may be readily provided to treat soil with superheated steam or other working fluid for reducing or eliminating unwanted microorganisms in the soil. In this regard, FIG. 15 is a schematic diagram of such a farm implement and includes a plough or disc-type of apparatus 516 having a frame 518 coupled at one end thereof to a vehicle, such as tractor 520. The frame 518 includes a plurality of rotatable discs 522 (one shown in FIG. 15) each having a central hub or manifold 524 and a plurality of uniformly, circumferentially spaced fingers 526. The fingers 526 may be configured similar to the distal end 510 of the adaptor 504 so as to penetrate the soil. One or more heater and steam generators, shown schematically at 528, may be mounted to the frame 518 for generating the superheated vapor-gas mixture (e.g., steam-air mixture) effective for reducing or eliminating unwanted microorganisms. For example, the heater and steam generator(s) 528 may be configured as described in the embodiments above. In operation, as the tractor 520 moves across the soil, the discs 522 rotate so that the fingers 526 penetrate into the soil. The fluid exiting the heater and steam generator(s) 528 flows out of the distal ends of the fingers and into the soil when located therein so as to reduce of eliminate microorganisms at least adjacent the soil-embedded finger. The apparatus 516 may then be used to treat a significant amount of soil, such as that typical of growing crops. It is believed that the apparatus 516 will result in the positive benefits above, but on a larger scale. For example, apparatus 516 may be suitable for treating soil for growing crops and other plant life typically grown on a large-scale basis. In another embodiment (not shown), a rake-like apparatus, which may have rotating features, may be used to treat the soil with superheated steam.

In a further embodiment in accordance with the invention, the soil that is treated with the superheated steam may be packaged for retail sale to the consumer. More particularly, fresh natural soil or alternatively a specialty soil, such as Miracle Grog, may be sterilized, disinfected, or otherwise treated in accordance with the embodiments described above. This sterilization of the soil may be done in a batch type of mode or in a continuous type of mode, such as with a continuous conveyor system that passes the soil by one or more heater and steam generators as described above. The treated soil may optionally be combined with additional nutrients and packaged in, for example, plastic bags for sale at various retail locations.

From the above disclosure of the general principles of the present invention and the preceding detailed description of various embodiments, those skilled in the art will readily comprehend the various modifications to which this invention is susceptible. For example, while many of the above embodiments describe the reduction or elimination of unwanted microorganisms using wet heat sterilization or disinfecting, (e.g., a superheated vapor of a working fluid), the invention is not so limited. In particular, embodiments of the invention may also implement dry heat sterilization or disinfecting. In this regard, the heated gas from the various apparatus is, in essence, the working fluid for microorganism destruction. The operational temperatures and/or the treatment times of the various apparatus may increase using dry heat. Nevertheless, although the preferred method for microorganism management is wet heat, dry heat may also be used to manage microorganisms associated with items. Therefore, we desire to be limited only by the scope of the following claims and equivalents thereof.

We claim:

1. An apparatus for generating a superheated fluid capable of reducing or eliminating microorganisms associated with an item, comprising: an electric heater for heating a gas; a superheated fluid generator operatively coupled to the electric heater and including a first fluid reservoir for supplying a first working fluid to the apparatus, wherein the electric heater heats the gas to a temperature above the saturation temperature of the first working fluid such that when the first working fluid is combined with the heated gas, the apparatus at least initially generates a mixture of superheated vapor of the first working fluid and the gas capable of reducing or eliminating microorganisms associated with the item, wherein the fluid generator further comprises: a jacket housing disposed about at least a portion of the electric heater and in thermal communication therewith, the housing defining a chamber having an inlet in fluid communication with the reservoir and an outlet in communication with the heated gas from the electric heater, wherein the first working fluid in the chamber of the housing is heated by the electric heater and then introduced to the heated gas via the outlet so as to generate the mixture of the superheated vapor of the first working fluid and the gas, the generation of the superheated vapor of the first working fluid and the gas occurring at approximately one atmosphere of pressure.

2. The apparatus of claim 1, wherein the first working fluid is selected from the group consisting of water, chemical cleaning agents, or combinations thereof.

3. The apparatus of claim 1, wherein the electric heater further comprises: a tubular enclosure having a gas entry port spaced from a gas exit port; an inner helical electric heating coil contained within the tubular enclosure; and an outer helical electric heating coil contained within the tubular enclosure and surrounding the inner coil to define a substantially unobstructed annular space between the coils.

4. The apparatus of claim 1, wherein the fluid generator further comprises: a reactor vessel for mixing the first working fluid from the reservoir with heated gas from the electric heater so as to generate the superheated vapor and gas mixture.

5. The apparatus of claim 1, wherein the apparatus is handheld and comprises: a housing member having an upper housing portion and a handle portion, the upper housing portion adapted to carry the electric heater and the fluid generator, the handle portion adapted to be grasped by a user.

6. The apparatus of claim 5, further comprising: a fan for supplying air to the electric heater.

7. The apparatus of claim 5, further comprising: a heat shield surrounding at least a portion of the housing member and configured to be grasped by a user.

8. The apparatus of claim 5, further comprising: an adaptor having a first end adapted to be coupled to the apparatus so that the superheated vapor and gas mixture enters the adaptor and a second end adapted to be inserted into a medium, wherein the superheated vapor and gas mixture flows through the second end of the adaptor and into the medium to reduce or eliminate microorganisms in the medium.

9. The apparatus of claim 1, further comprising: a second fluid reservoir operatively coupled to the apparatus for supplying a second working fluid to the apparatus.

10. The apparatus of claim 9, wherein the second working fluid is introduced into the gas heater and prior to mixing the gas with the first working fluid.

* * * * *

UNITED STATES PATENT AND TRADEMARK OFFICE
CERTIFICATE OF CORRECTION

PATENT NO. : 8,435,459 B2  Page 1 of 2
APPLICATION NO. : 12/514516
DATED : May 7, 2013
INVENTOR(S) : Ganta S. Reddy, Ramgopal Vissa and Jainagesh Sekhar It is certified that error appears in the above-identified patent and that said Letters Patent is hereby corrected as shown below:

In the Drawings

Replace incorrect drawing sheet with attached corrected sheet containing drawing sheet 15.

Signed and Sealed this
Twenty-fifth Day of February, 2014

Michelle K. Lee
*Deputy Director of the United States Patent and Trademark Office*